(12) United States Patent
Anhold

(10) Patent No.: US 11,990,240 B2
(45) Date of Patent: May 21, 2024

(54) SYSTEM AND METHOD FOR OPTIMIZING PATIENT-SPECIFIC INTERVENTION STRATEGIES USING POINT OF CARE DIAGNOSTICS

(71) Applicant: Heinrich Anhold, Sligo (IE)

(72) Inventor: Heinrich Anhold, Sligo (IE)

( * ) Notice: Subject to any disclaimer, the term of this patent is extended or adjusted under 35 U.S.C. 154(b) by 31 days.

(21) Appl. No.: 17/094,606

(22) Filed: Nov. 10, 2020

(65) Prior Publication Data
US 2021/0110929 A1 Apr. 15, 2021

Related U.S. Application Data

(63) Continuation of application No. 13/170,984, filed on Jun. 28, 2011, now Pat. No. 10,867,701.

(60) Provisional application No. 61/479,264, filed on Apr. 26, 2011, provisional application No. 61/359,304, filed on Jun. 28, 2010.

(51) Int. Cl.
G16H 50/20 (2018.01)
G16H 50/70 (2018.01)

(52) U.S. Cl.
CPC .............. *G16H 50/20* (2018.01); *G16H 50/70* (2018.01)

(58) Field of Classification Search
CPC ........ G16H 50/20; G16H 50/70; G16H 20/00; G16H 40/67; G16H 50/30; G16H 80/00; G16H 10/40
See application file for complete search history.

(56) References Cited

U.S. PATENT DOCUMENTS

| | | |
|---|---|---|
| 6,168,563 B1 | 1/2001 | Brown |
| 6,245,818 B1 | 6/2001 | Lignell |
| 6,270,455 B1 | 8/2001 | Brown |
| 6,966,880 B2 | 11/2005 | Boecker |

(Continued)

FOREIGN PATENT DOCUMENTS

WO  WO-2009063285 A1 * 5/2009 ......... G06F 19/3443

OTHER PUBLICATIONS

"Philips breakthrough Magnotech technology set to transform global point-of-care testing", http://www.research.philips.com/newscenter/archive/2008/081119-magnotech-medica.html, 3 pages, published on Nov. 20, 2008.

(Continued)

*Primary Examiner* — Eliza A Lam
(74) *Attorney, Agent, or Firm* — TUCKER ELLIS LLP

(57) ABSTRACT

Described herein is a system and method for optimizing patient-specific intervention strategies using point of care diagnostics. In accordance with an embodiment, the system allows for biological sampling in a portable or point of care device, and generation of healthcare data wherein instantaneous results have value at a particular location for emergency care, improvement of overall healthcare, fitness and/or disease management, or to provide an economic value. In accordance with an embodiment, the system can be used to evaluate a biological sample, and optionally guide a user, such as a medical professional or carer through inputting or retrieving additional objective and/or subjective observations and/or retrieving historical medical information for the patient. The system can use various inputs to generate status and performance indications, such as whether a patient seems in good or poor health, or is particularly likely to perform well, or not.

20 Claims, 22 Drawing Sheets

(56) References Cited

U.S. PATENT DOCUMENTS

| | | | |
|---|---|---|---|
| 7,558,622 B2 | 7/2009 | Tran | |
| 7,575,558 B2 | 8/2009 | Boecker | |
| 7,797,145 B2 | 9/2010 | Dodds | |
| 7,912,734 B2 | 3/2011 | Kil | |
| 7,987,100 B2 | 7/2011 | Brown | |
| 8,005,692 B2 | 8/2011 | Karkanias | |
| 8,140,143 B2 | 3/2012 | Picard | |
| 8,758,245 B2 * | 6/2014 | Ray | G16H 20/10 600/347 |
| 10,867,701 B1 | 12/2020 | Anhold | |
| 2003/0073931 A1 | 4/2003 | Boecker | |
| 2004/0260204 A1 * | 12/2004 | Boecker | A61B 5/1519 600/584 |
| 2005/0228692 A1 | 10/2005 | Hodgdon | |
| 2006/0222567 A1 * | 10/2006 | Kloepfer | G01N 33/558 422/68.1 |
| 2007/0136355 A1 | 6/2007 | Haider | |
| 2007/0276270 A1 | 11/2007 | Tran | |
| 2008/0147441 A1 | 6/2008 | Kil | |
| 2008/0208620 A1 | 8/2008 | Karkanias | |
| 2009/0216105 A1 * | 8/2009 | Drucker | G16H 40/67 604/48 |
| 2010/0310423 A1 | 12/2010 | Nieuwenhuis | |

OTHER PUBLICATIONS

Wired, "The blood test gets a makeover", published to http://www.wired.com/2010/11/ff_bloodwork/all/1, 17 pages, published on Nov. 29, 2010. (Downloaded on May 12, 2016.).

Bruls, D.M. et al., Rapid integrated biosensor for multiplexed immunoassays based on actuated magnetic nanoparticles, Philips Corporate Technologies, Lab on a Chip, Oct. 15, 2009, issue 24, pp. 3504-3510, 7 pages.

The Irish Times, "Sligo firm devising handheld reader", http://www.irishtimes.com/business/sligo-firm-devising-handheld-reader, 2 pages, published on Dec. 17, 2010. (Downloaded on May 12, 2016.).

The Irish Times, "Irish company to trial blood testing device for horses", Caroline Madden, http://www.irishtimes.com/business/technology/irish-company-to-trial-b, 2 pages, published on Aug. 26, 2011. (Downloaded on May 12, 2016.).

The Irish Times, "Seeds of a fresh start", http://www.irishtimes.com/business/2.790/seeds-of-a-fresh-start-1.1279, 3 pages, published on Jan. 28, 2011. (Downloaded on May 12, 2016.).

"Magnotech: Philips' magnetic biosensor platform designed for point-of-care testing", http://www.newscenter.philips.com/main/standard/news/backgrounders/2010/20100107_magnetic_biosensor.wpd, 5 pages, published on Jan. 7, 2010.

Technology Ireland: issue 5, vol. 41, "Horse Sense", Nov./Dec. 2010, pp. 28-30, 3 pages.

"Thomas Goetz: It's time to redesign medical data", published to http://www.ted.com/talks/thomas_goetz_it_s_time_to_redesign_medical_data, filmed Oct. 2010, 7 pages. (Downloaded on May 12, 2016.).

"Thomas Goetz: It's time to redesign medical data", http://www.ted.com/talks/thomas_goetz_it_s_time_to_redesign_medical_data/transcript?language=en, 7 pages, published in Oct. 2010. (Downloaded on May 12, 2016.).

United States Patent and Trademark Office, Office Communication dated Dec. 12, 2017 for U.S. Appl. No. 13/170,984, 15 pages.

United States Patent and Trademark Office, Office Communication dated Nov. 2, 2018 for U.S. Appl. No. 13/170,984, 13 pages.

United States Patent and Trademark Office, Office Communication dated Oct. 3, 2019 for U.S. Appl. No. 13/170,984, 14 pages.

United States Patent and Trademark Office, Notice of Allowance and Fee(s) Due dated Jul. 29, 2020 or U.S. Appl. No. 13/170,984, 6 pages.

* cited by examiner

FIGURE 4

SYSTEM AND METHOD FOR OPTIMIZING PATIENT-SPECIFIC INTERVENTION STRATEGIES USING POINT OF CARE DIAGNOSTICS

CLAIM OF PRIORITY

This application is a continuation of U.S. patent application titled "SYSTEM AND METHOD FOR OPTIMIZING PATIENT-SPECIFIC INTERVENTION STRATEGIES USING POINT OF CARE DIAGNOSTICS", application Ser. No. 13/170,984, filed Jun. 28, 2011; which application claims the benefit of priority to U.S. Provisional patent application titled "PORTABLE SYSTEM FOR CLINICAL AND PERFORMANCE EVALUATION OF EQUINES AND OTHER ANIMALS", Application No. 61/359,304, filed Jun. 28, 2010; and U.S. Provisional patent application titled "SYSTEM AND METHOD THAT COMBINES BLOOD RESULTS WITH PATIENT-SPECIFIC INFORMATION TO CREATE CUSTOMIZED REFERENCE POINTS", Application No. 61/479,264, filed Apr. 26, 2011; each of which above applications are herein incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

Embodiments of the invention are generally related to animal and human healthcare, and are particularly related to systems and methods for the collection and analysis of point of care diagnostic results from biological samples, and their use in clinical and performance evaluation, such as assessing how a subject or patient's biological sample diagnostic results might be affected by specific nutritional and exercise interventions.

BACKGROUND

Healthcare-related data has traditionally been presented in formats that are quite technical, and provide little or no context relative to an individual patient. Part of the challenge is that patients are broadly grouped and diagnosed by particular standards. For example, common blood results are given 'reference ranges' within which the patient's blood results are deemed to be 'normal' and provides little context relevant to the individual patient. Also, dosages of drugs and nutraceuticals are often prescribed irrespective of the patient's physical status, exercise levels or individual characteristics. To this end, it is often left to the medical or healthcare professional to interpret patient information within a particular context and to decide upon effective intervention strategies, which has been shown to be highly subjective. In an animal healthcare setting, the patient is often outside of the care of the medical professional, making effective interventions even more challenging.

Current methods rely heavily on the knowledge and experience of the medical professional, and his/her ability to communicate patient information. This means there is a wide variation in the quality of healthcare services. In many instances, the effectiveness of medical intervention has been shown to be improved when the patient is well informed (or the carer in an animal healthcare context) and is involved in the decision making process for effective intervention. Furthermore, the use of algorithms together with medical opinion can be more effective than relying on medical opinion alone. Better organization and communication of healthcare information may provide a more accurate diagnosis, and a more effective intervention strategy.

Animal healthcare generally relates to the evaluation and care of non-human animals, including assessment of the animal's physiology and other characteristics pertaining to the animal's health. Industries such as the equine (horse breeding) industry, food animal industry, and companion animal industry, form significant sectors of the developed world's economies. In recent years, the spread of animal diseases has caused major health, economic and social difficulties on a global scale, and has brought the issue of animal healthcare to the forefront. Common aspects of animal healthcare include routine physical examinations, health checks and biological sampling such as blood, urine or milk. In many instances, the veterinarian/carer is interested not just in the animal's current health status, but also in the animal's likelihood of future performance, for example, in an upcoming horse race or quality milk yield in a dairy herd. Clinical testing, such as biological sampling and evaluation, can be used to provide an indication of the animal's overall physiology and to derive intervention strategies for improving health and performance.

For both human and non-human patients, the currently methodology of obtaining, interpreting and intervening upon biological sample diagnostic results involves many stages and actors and can include long periods of delays. For example obtaining blood diagnostic results from a horse may involve an animal carer, a veterinarian, a laboratory technician and various modes of communication in between including postal, facsimile, email and/or phone. The time delay between sample collection and intervention can therefore range from minutes to days depending on the available resources. The quality of the medical care that the patient receives depends upon the efficiency and competency of each stage and each actor. As a net result of the current methodology few patients, either animal or human, receive the best available intervention strategies.

These are the general areas that embodiments of the present invention are designed to address.

SUMMARY

Described herein is a system and method for optimizing patient-specific intervention strategies using point of care diagnostics. In accordance with an embodiment, the system allows for biological sampling in a portable or point of care device, and can allow for generation of healthcare data wherein instantaneous results have value at a particular location for emergency care, improvement of overall healthcare, fitness and/or disease management, or to provide an economic value. In accordance with an embodiment, the system can be used to evaluate a biological sample such as for example a blood sample, milk sample, or urine sample and relates to the current status of a subject/patient, and optionally guide a user, such as a medical professional or carer through inputting or retrieving additional objective and/or subjective observations and/or retrieving historical medical information for the patient. Also described herein is a system and method for the creation of individual reference points that relate to a specific physical condition in that individual patient. The system can use the various inputs to generate status and performance indications, such as whether a patient seems in good or poor health, or is particularly likely to perform well, or not.

BRIEF DESCRIPTION OF THE FIGURES

FIG. 4 illustrates some examples of results communication, in accordance with an embodiment.

DETAILED DESCRIPTION

Figure 1:
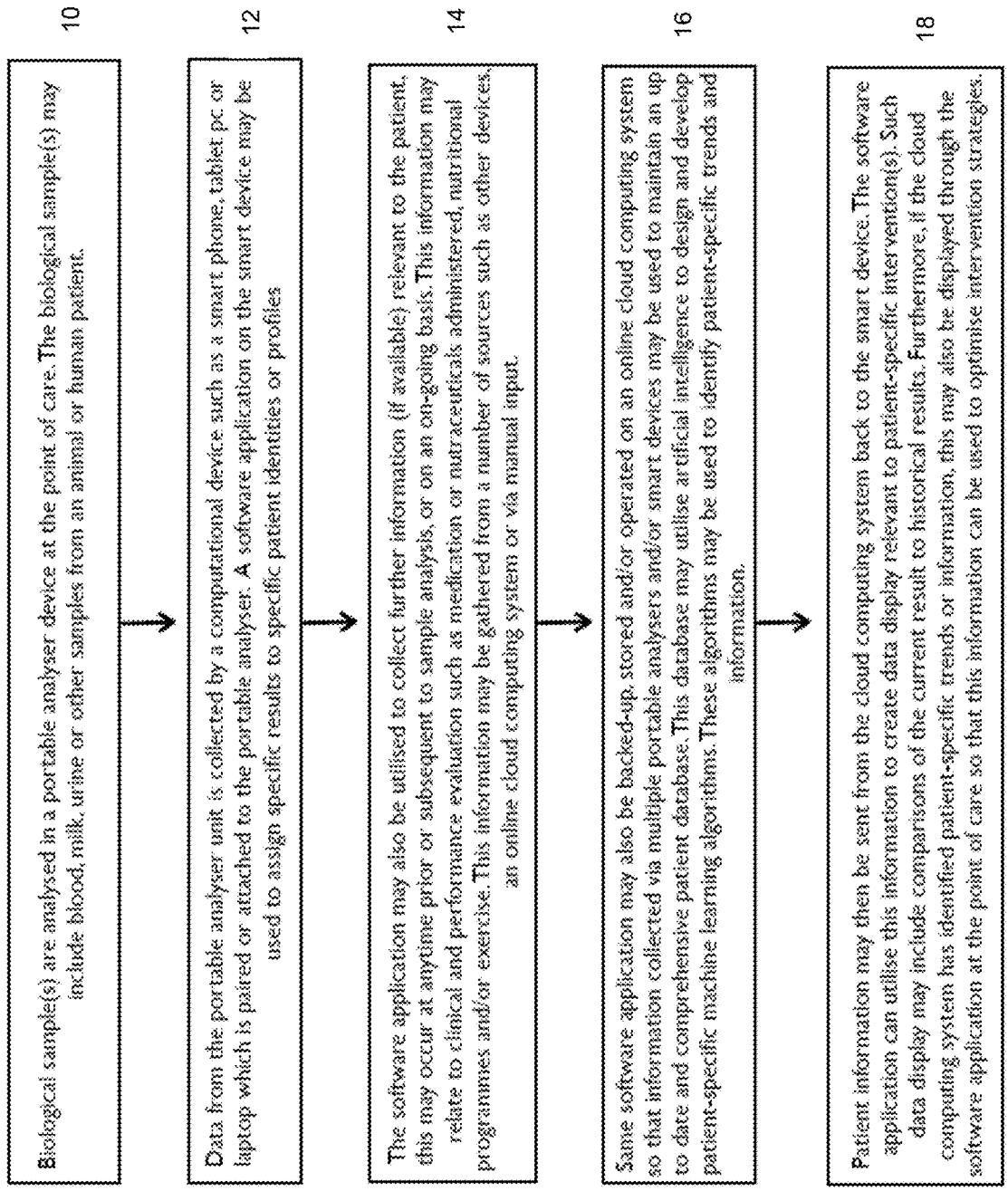
FIG. 1 shows an illustration of the steps used to optimize patient-specific intervention strategies, in accordance with an embodiment.

As described above, the currently methodology of healthcare-related testing using biological sampling is to send a sample to an off-site laboratory, for example, a hospital or centralized laboratory, where it is analyzed by experienced technicians and pathologists using bench-top equipment. However, current laboratory testing processes do not adequately serve the healthcare industry, including the animal healthcare industry, since in many instances the patient and their carer are dispersed in rural or remote locations, away from advanced infrastructure, and within many jurisdictions legislation prevents the laboratory from dealing with the animal carer directly, so therefore all samples and data/information must pass through various actors and stages before a decision upon intervention can be made. Clinical testing which includes blood, urine or milk analysis can take a long period of time, due to the need to send blood samples long distances and then wait for the results to be returned. Such delays can have significant consequences, both in terms of the patient's health and general economics. Furthermore, when data arrives back to the medical professional and/or carer it may not be used in the most effective manner as data interpretation can be carried out in the absence of patient specific information and may be highly subjective. This methodology does not allow for the most meaningful intervention for the individual patient.

Described herein is a system for optimizing patient-specific intervention strategies using point of care diagnostics. In accordance with an embodiment, the system allows for biological sampling in a portable or point of care device, and can allow for generation of healthcare data wherein instantaneous results have value at a particular location for emergency care, improvement of overall health, fitness and disease management, or to provide an economic value. In accordance with an embodiment, the system can be used to evaluate a blood sample, urine sample or milk sample for cell count, enzyme, protein, and lipid quantification and/or other tests related to the current status of a subject/patient, and optionally guide a user, such as a medical professional or carer through inputting or retrieving additional objective and/or subjective observations and/or retrieving historical information for the patient. The system can use the various inputs to generate status and performance indications, such as whether a patient/subject seems in good or poor health, or is particularly likely to perform well, or not.

Also described herein is a system and method for customization of biological sample reference ranges to individual patients, so as to present these results in a customized manner specific to the individual patient, or allow for the creation of individual reference points that relate to a specific physical condition in that individual patient. For example, in a veterinarian or equine setting, a horse may be recognized by its trainer as being in peak fitness. The trainer can record and store a blood result at that time as a set of reference points for the horse when it is in that particular physical state. Variations and fluctuations from these reference points may indicate that the horse has now deviated from its physical condition of peak fitness.

Introduction

Within the healthcare industry, including both animal and human healthcare, the need for relevant point of care diagnostics, sophisticated management systems, and rapid effective intervention is an obvious matter of urgency. For example, pandemics caused by animal-borne viruses have caused major negative economic and social impacts. In the context of veterinary care, the lack of rapid assessment and intervention in general animal healthcare leads to much undue suffering by animals, and adds burden and costs to carers. Furthermore, carers who rely on getting the most value from their stock currently lack the diagnostic tools necessary to achieve optimum performance from their animals.

Blood cell counting, ratios of particular blood cells, and classification of blood cells can provide valuable insight into many aspects of animal health. From measurement of anemia, to immune system response, and to specific disease diagnosis such as for example mastitis, blood cell counting and classification can be used in a variety of significant diagnostic tests.

Other blood and biological sample information can have particular relevance to specific organ function and specific medical conditions. For example, muscle and liver enzymes in horses can be used for the detection and management of equine exertional rhabdmyolysis also known as 'tying-up'.

Currently, in many healthcare settings, by the time the biological sample diagnostic results are received from the laboratory, the medical professional/carer has moved on from dealing with that particular patient. In the intervening period, between collecting the sample and obtaining the results, many factors can influence the patient's status, and therefore the results often have little or no benefit by the time they are delivered.

Embodiments of the present system allow the biological sample analysis to occur at the patient's side, despite the location of the patient. Additionally, the user can input and/or retrieve further information, relating to intervention, in real-time relative to the analysis. Information relating to intervention, may fall under the headings of; medication, nutritional and/or nutraceutical and exercise, and may be generated by the user directly or be collected from another source e.g. an online cloud computing database. Therefore, the intervention data collected and/or inputted by the user has a high relevance to the biological sample data, and can build on the diagnostic outcome, ultimately leading to an improved outcome of referral or intervention.

Described herein is a system and method for data input from the user either at the time of biological sample analysis or indeed in the period of time leading up to or subsequent to the biological sample analysis. For example, a racehorse trainer may record and input animal details such as training information (distance ran and split times). The trainer may then collect and analyze a blood sample from that horse using a point of care blood analyzer. Subsequent to the time of blood analysis same trainer may then record further performance details of same horse during another training session.

As disclosed herein, in accordance with an embodiment, is a system and method for analysing biological samples, for example, blood, urine or milk, using a portable or point of care analyzer unit.

As further disclosed herein, in accordance with an embodiment, is a system and method for transforming signals, generated from biological samples, into data that can be validated, manipulated, transmitted or presented and used for immediate referral or intervention at the animal's side.

As further disclosed herein, the system and method allows for concurrent collection of data from biological samples and data input and collection by the user at the patient's side.

As further disclosed herein, the system and method allows for the use of a software application to collect data from the portable analyzer unit and transform signals, generated from biological samples, into data that can be validated, manipulated, transmitted or presented and used for immediate referral or intervention at the animal's side.

As further disclosed herein, the system and method allows for concurrent collection of data from biological samples and data from an online cloud computing database.

As further disclosed herein, the system and method can be used in the context of general healthcare, for example, in a rural location, in a patient's home, in a veterinary clinic, at the premises of an animal owner, in an animal barn, in a dairy parlor, in a meat factory, in a transport vehicle, at a port or border checkpoint, or in a research facility. In the context of equine healthcare for example, this can in a stable, in an open pen, on a horse trailer, at a racing track or at a sporting event.

Biological samples can be analyzed via embedded technology within a portable machine adapted for point of care analysis. The system is also flexible in that it allows for transformation of signals created from biological samples at the point of use to a smart device or multiple smart devices such as mobile phones, PDA's or tablet computers.

Using the smart device the data can then be, manipulated, transmitted or presented, at the point of use or at multiple remote locations in real-time to the analysis.

Transmitting healthcare information, including biological sample diagnostic results, to an online cloud computing system, can allow for the generation of patient healthcare databases. Furthermore, such databases can implement machine learning artificial intelligence systems for the design and development of novel algorithms. Such algorithms can be patient specific and can for example be used to establish individual patients trends and responses to interventions. In the case of a horse which is prone to equine exertional rhabdomyolysis (EER), factors that may influence the onset of EER can be identified in advance of an episode, or interventions used to treat a horse after an episode can be established as having a positive effect, or not.

The online cloud computing database can also be utilised by the smart device to recall patient information, such as historical results, so that trends can be displayed in real-time at the patients side, at the time of biological sample analysis.

Embodiments of the system and method are particularly useful in home monitoring of patients with chronic diseases.

Embodiments of the system and method are particularly useful in the economics and efficiency of animal healthcare for the control and monitoring of animal diseases.

Embodiments of the system and method are particularly useful in the generation of meaningful interventions that are specific to the individual (human or non-human) patient.

Embodiments of the system and method are particularly useful in athletes, for example in equine healthcare for training and management of racehorses and the optimization and analysis of racehorse performance.

In accordance with an embodiment, the system can include a machine for biological sample analysis, a computing device including but not limited to a computer, a smartphone or a mobile tablet computing device, a cloud computing system database and immediate analysis of patient specific data.

In accordance with an embodiment that utilizes a machine, the method can incorporate a combination of technologies including but not limited to chemical technologies, fluidic technologies, electrical detection technologies, optical detection technologies, electromagnetic technologies, software or computer based technologies. Biological samples collected from a patient can be immediately analyzed at the point of care and transformed into manageable data. Such data to be immediately recorded, validated, manipulated, stored, or presented within the portable machine or transmitted to a computing device where the data can be recorded, validated, manipulated, stored, or presented and/or transmitted to a cloud computing system whereby the data can be recorded, validated, manipulated, stored, or presented at single or multiple other locations.

In accordance with other embodiments the system can also be used as part of an overall patient health, wellness, fitness or disease management system.

In accordance with an embodiment, described herein is a system and method for patient-specific data collection whereby further information relating to interventions is inputted and/or collected from a database or other device. Such information may relate to medical interventions, nutritional and/or nutraceutical interventions or exercise and training interventions.

In accordance with an embodiment, described herein is a system and method for data analysis whereby data can be stored for historical or categorical organization of results.

As further disclosed herein, the system allows for the generation of patient databases. Such databases may be used for the design and development of algorithms using, for example, machine learning artificial intelligence.

In accordance with an embodiment the system comprises a collection of components, which depending on the particular implementation, may be used together as part of an overall system or process. Alternatively, a selection of one or more of the components can be employed to handle certain tasks. Additional components can then be added to the system as necessary. In accordance with an embodiment, components may include:

Point of Care Analyzer Unit, is a machine comprised of mainly electrical components, and may or may not involve a lab on a chip technology. The point of care analyzer is used to carry out biological sample analysis at the point of care. In addition, the point of care analyzer unit is used to transform, e.g., electrical or optical signals, which are representative of biological samples into quantifiable data and may be further used to transmit this data to a computational device.

Computational device, which may be a computer, smartphone, tablet computer or other suitable device and is used to manage results data, for example data can be immediately recorded, validated, manipulated, stored, or presented through a software application or transmitted to a cloud computing system whereby the data can be recorded, validated, manipulated, stored, or presented at single or multiple other locations. The computational device can also be used to collect further information relating to the patient, for example, data relating to interventions and historical results data. This further information can be collected from the user directly through manual input or from a range of other devices or from an online cloud computing database.

Software application, which synchronizes (syncs) information with the online cloud computing database and allows for the user to interface with patient results. The software application can also be used to collect further information relating to the patient, for example, data relating to interventions and historical results data. This further information can be collected from the user directly through manual input or from a range of other devices or from an online cloud computing database. The software application can provide an easy to use interface allowing for clear presentation of results and access to results at any time via connection to the cloud computing database. Further functions of the cloud computing system may be to sync data with the point of care analyzer and allow for data to be recorded, validated, manipulated, stored, or transmitted to other devices.

Cloud computing system, used as a database for patient information. The cloud computing system can also be used to design and develop novel algorithms that may or may not be patient specific. Novel algorithms may be designed and developed through a machine learning artificial intelligence system held on the cloud. The novel algorithms may be held on the cloud or transmitted to the software application for direct use on the computational device.

As described in further detail below, the above components can be used collectively to provide a system and method for analyzing biological samples, using a portable machine, as well as a system for transforming signals, generated from biological samples, into data that can be validated, manipulated, transmitted or presented and used for immediate referral or intervention at the patient's side.

Portable System for Generating Patient-Specific Information at the Point of Care FIG. 1 shows an illustration of the steps used to optimize patient-specific intervention strategies, in accordance with an embodiment. As shown in FIG. 1, in step 10, biological sample(s) are analyzed in a portable analyser device at the point of care. The biological sample(s) may be blood, milk, urine or other samples from an animal or human patient. In accordance with an embodiment, the portable analyzer device is employed by a user or carer (e.g., a medical professional, trainer, owner, veterinarian, or other user), to collect data from a biological sample from the subject/patient. In an animal or human context, the biological sample collection usually requires that a sample such as a blood, milk or urine sample be taken from an animal, which may or may not be analysed using lab on chip technology.

For point of care use the sample is generally taken immediately before the analysis. In some instances the sample may be stored for a certain period of time before analysis, or may be required to be analyzed in a different location to the animal. For example, a blood sample may be taken from a nervous or dangerous horse in a stable or closed environment, in which instances the user or carer may wish to vacate the stable before taking the time required to carry out the analysis. In a dairy parlor, milk samples are generally collected during the milking process by attaching a particular device such as a 'milk recorder supply' which can obtain a composite throughout the period of milking and may then be analyzed subsequent to milking.

In step 12, the data generated from the portable analyzer device is synced or transferred to a computational device such as a smart phone, tablet computer or laptop computer. This transfer may occur through a physical connection such as a wire or may occur wirelessly via Bluetooth, WiFi or other suitable system. Using a software application the smart device is then able to assign relevant data to individual patient identification for organization and storage.

In step 14, additional patient-specific data and information is collected. This may occur using the computational device and software application directly or alternatively may occur through a cloud computing system, whereby the cloud computing system collects data from one or multiple other sources. Additional patient-specific data and information may include but not be limited to; medication, nutritional information, training and exercise information and additional biological sample diagnostic information. Subjective observations of the patient/subject's physiological and behavioral characteristics, from a medical professional and/or carer (such as a farmer or racehorse trainer) can also be included.

In step 16, a patient-specific database is generated and maintained on a cloud computing system. All patient information, regardless of source, is sent to and stored in an online database. This database is continuously updated as new data is generated. Data may be generated from the portable analyzer device, computational device or other suitable systems and devices. The database may then be utilized by artificial intelligence systems to design and develop machine learning algorithms that are patient-specific.

For example, in the case of a horse that is prone to equine exertional rhabdmyolysis (EER), onset of an episode may be attributed to a particular combination of diet, exercise and muscle enzyme levels. This particular pattern or combination of interventions can be identified and characterized by the machine learning system. When the particular characteristic pattern is identified to re-occur, an alert may be communicated to the horse's carer in order to attempt to prevent a repeat episode. For example this may be the detection of elevated level of creatinine kinase from an equine blood sample subsequent to a prolonged period of exercise in combination with a specific diet. If such a pattern is identified an alert may be sent to the animal carer at the point of care and at the time of blood sample analysis so as to immediately intervene and prevent a repeat episode of EER.

In step 18, the computational device is again used, this time specifically for data communication. Utilizing the online database the software application is able to present the most up to date patient-specific trends and information. For example, a blood cell count may be presented alongside the two most recent cell count results to indicate whether a particular cell population is either increasing or deceasing in number. Furthermore, the user may be able to recall previous intervention strategies used on the individual patient/subject and obtain data on their effectiveness on that specific patient, all at the point of care and at the time of biological sample analysis. The system and method thus adds context to a point of care results via historical comparisons and patient-specific interventions which can be utilized at the patient/subject's side.

In accordance with an embodiment, the software application can utilize this information to create data display relevant to patient-specific intervention(s). Such data display may include comparisons of the current result to historical results. Furthermore, if the cloud computing system has identified patient-specific trends or information, this may also be displayed through the software application at the point of care so that this information can be used to optimize intervention strategies.

Figure 2:
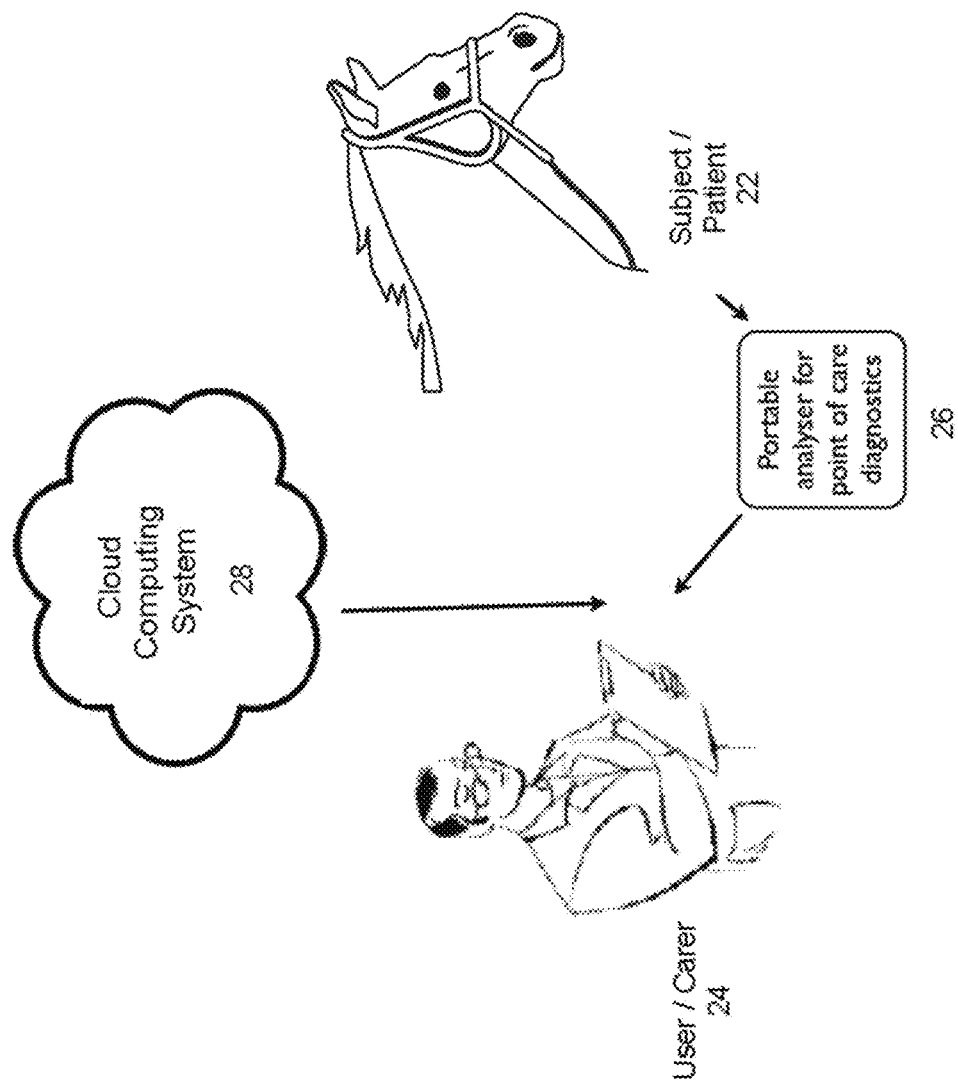
FIG. 2 shows an illustration of an environment that can be used to provide patient-specific information at the point of care, in accordance with an embodiment.

FIG. 2 shows an illustration of an environment that can be used to provide patient-specific information at the point of care, in accordance with an embodiment. As shown in FIG. 2, the process can be used with a subject/patient 22, such as a horse or other human or non-human animal, by a user or carer 24, such as a medical professional, trainer, owner, veterinarian, or other user. In accordance with an embodiment, a biological sample is analyzed from the subject/patient, using a machine such as a portable or point of care analyzer 26. In accordance with an embodiment, the user can analyze biological sample data via a computational device such as a smart phone, tablet computer or laptop computer. The computational device may simultaneously connect to the portable analyzer and an Internet-based cloud computing system 28. The user can also input additional observations about the subject/patient into the computational device. An analysis software or logic then uses the information from the portable analyzer, together with data from the cloud computing system, to provide an immediate output to the user via a user interface, which can include information about the subject's current health, status and performance indications. Key features of the system include instant or real-time biological sample analysis via the portable analyzer, assigning biological sample data to a specific patient's identification via the computational device, a patient-specific online database accessed on the cloud computing system via the computational device and point of care data display of current and historical patient information at the point of care via an embedded software application on the computational device.

Custom Result Reporting Using Reference Ranges/Points

Figure 3:
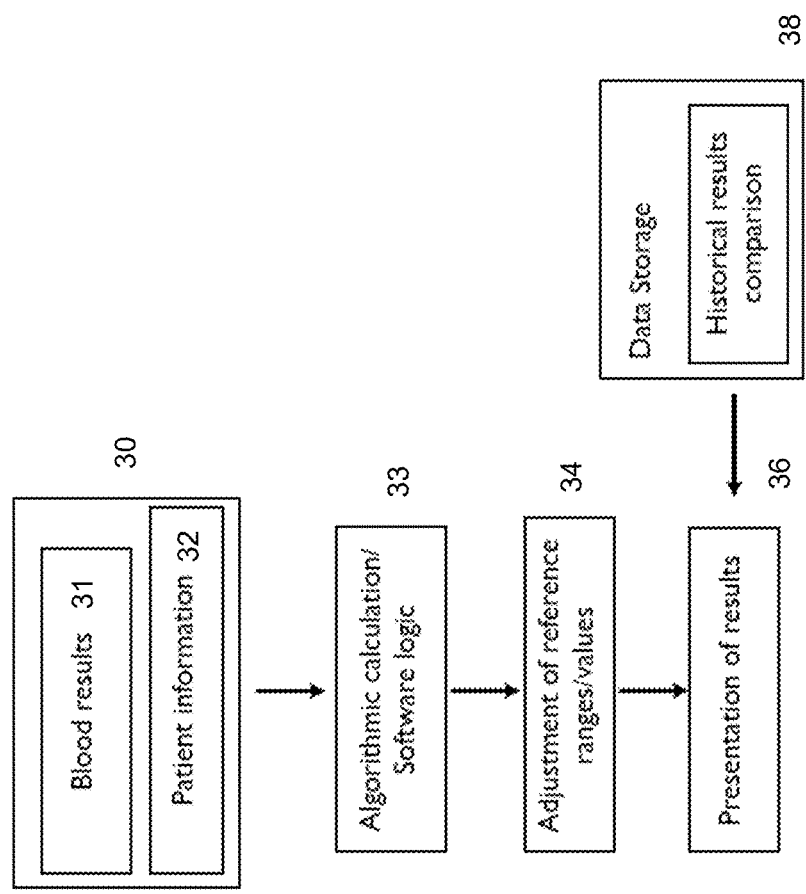
FIG. 3 illustrates the steps involved in generating customized patient results, in accordance with an embodiment.

FIG. 3 illustrates the steps involved in generating customized patient results, in accordance with an embodiment. As shown in FIG. 3, step 30 includes the collection of patient biological sample results 31 and information 32. This may be carried out, for example, using a software application embedded on a computational device as described above, smartphone, tablet computer or laptop computer. Steps 33 and 34 include the transformation of this data and information using a suitable software logic, which can include the use of mathematical algorithms. Such transformation allows for both the data and the patient information to influence the display of results. Step 36 includes a presentation of results for clear and accurate communication of healthcare information. Step 38 is an additional step that may be optionally used to enhance step 36, and includes the use of historical patient blood results and information to add context to the current result. For example, this may be used to show trend information, or to predict an emerging pattern of data.

Figure 4:
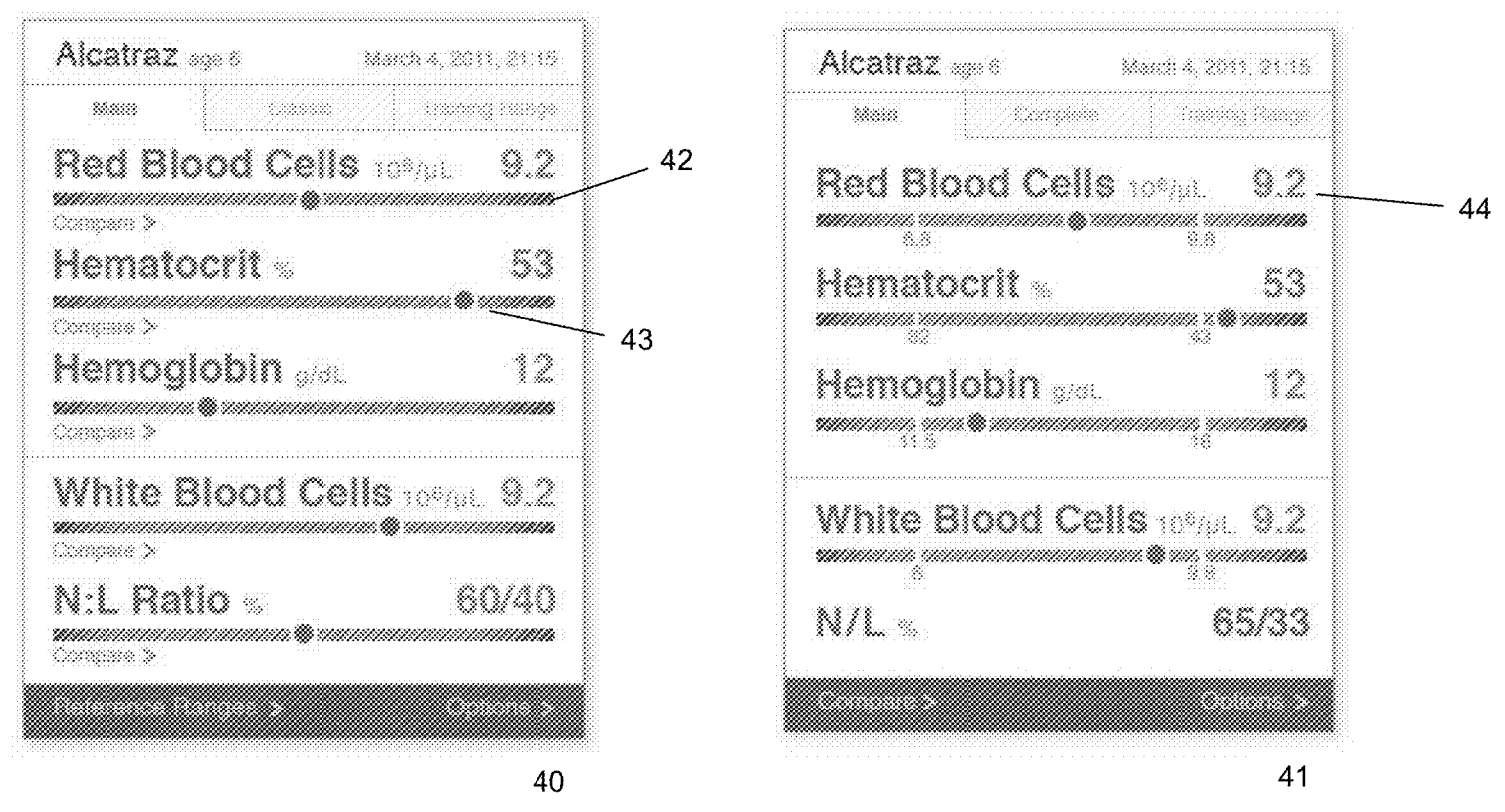

FIG. 4 illustrates some examples of results communication, in accordance with an embodiment. As shown in FIG. 4, information can be displayed (40, 41) to reflect how the blood results are relevant in the context of the individual patient. Reference points and ranges can be calculated based on patient information. The relevance of the blood results can then be presented and communicated via visual (42), graphical (43), and/or numerical or other representations (44).

Figure 5:
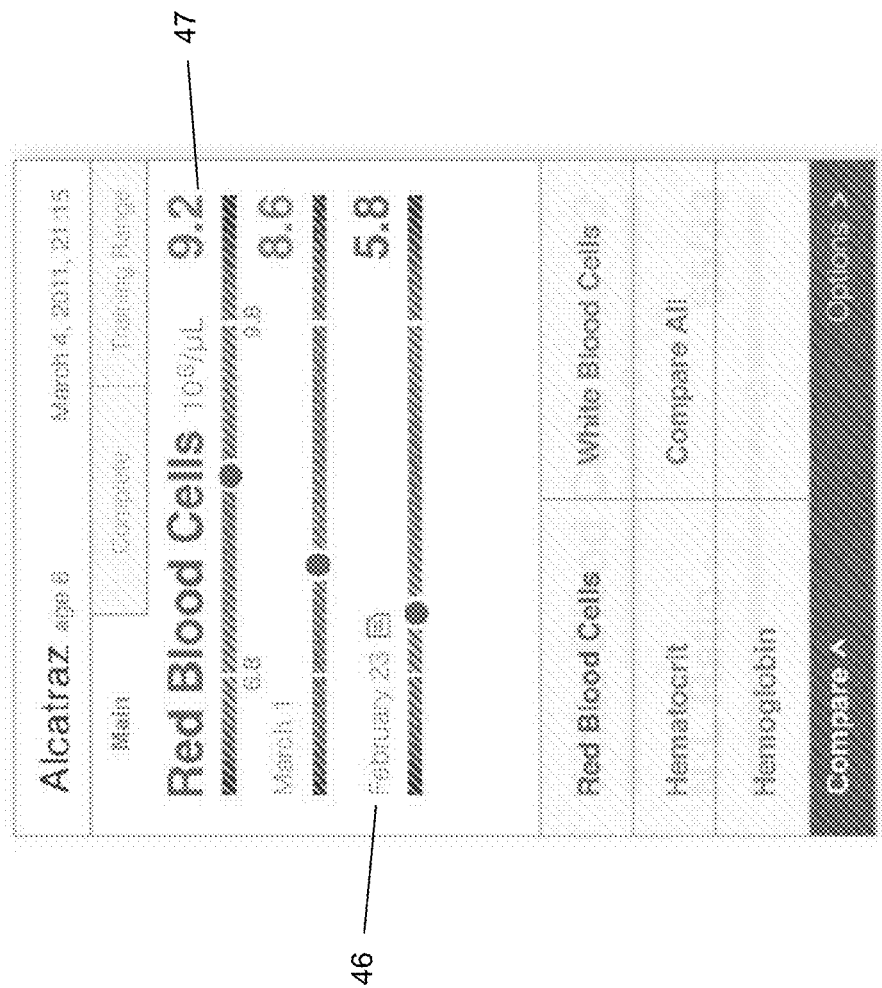
FIG. 5 illustrates an example of using historical results to add context to current results, in accordance with an embodiment.

FIG. 5 illustrates an example of using historical results to add context to current results, in accordance with an embodiment. As shown in FIG. 5, historical information (46) can be presented alongside current information (47), so that trends can be identified. In accordance with an embodiment such data and information can also be used over time to identify repeating patterns.

Figure 6:
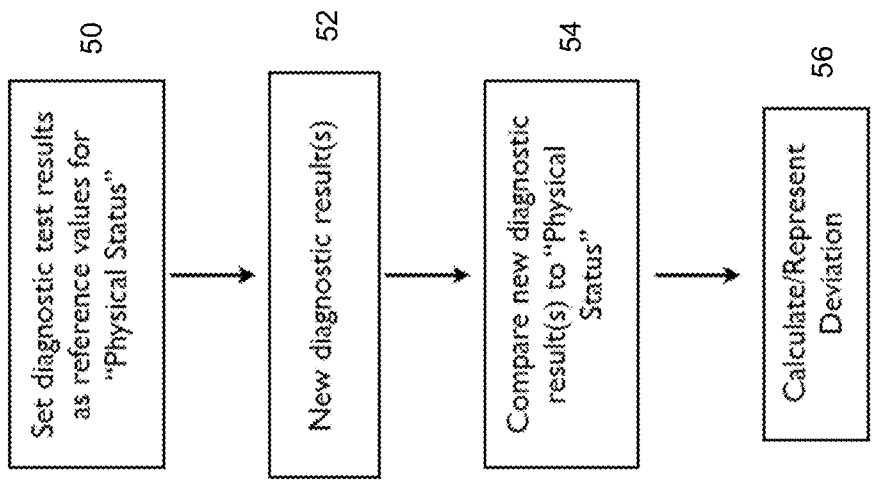
FIG. 6 illustrates the steps in establishing a set of reference values to represent an individual's physical status and the steps used to utilize these, in accordance with an embodiment.

FIG. 6 illustrates the steps in establishing a set of reference values to represent an individual's physical status and the steps used to utilize these, in accordance with an embodiment. As shown in FIG. 6, step 50 includes carrying out a blood diagnostic to establish a result or set of results. In accordance with an embodiment, the result(s) may then be stored as a reference point(s) for a specific physical condition, for example, a patient with a stabilized medical condition or an athlete under physical training. Step 52 includes the generation of new biological sample diagnostic results, while step 54 includes the comparison of these new biological sample results to the reference value(s) for the desired physical status. Step 56 is not required in every embodiment, but optionally includes the mathematical calculation of the deviation of the new results from the physical status. This may be used for example, to identify deterioration in health, onset of disease or decreased physical fitness, in accordance with an embodiment.

Figure 7:
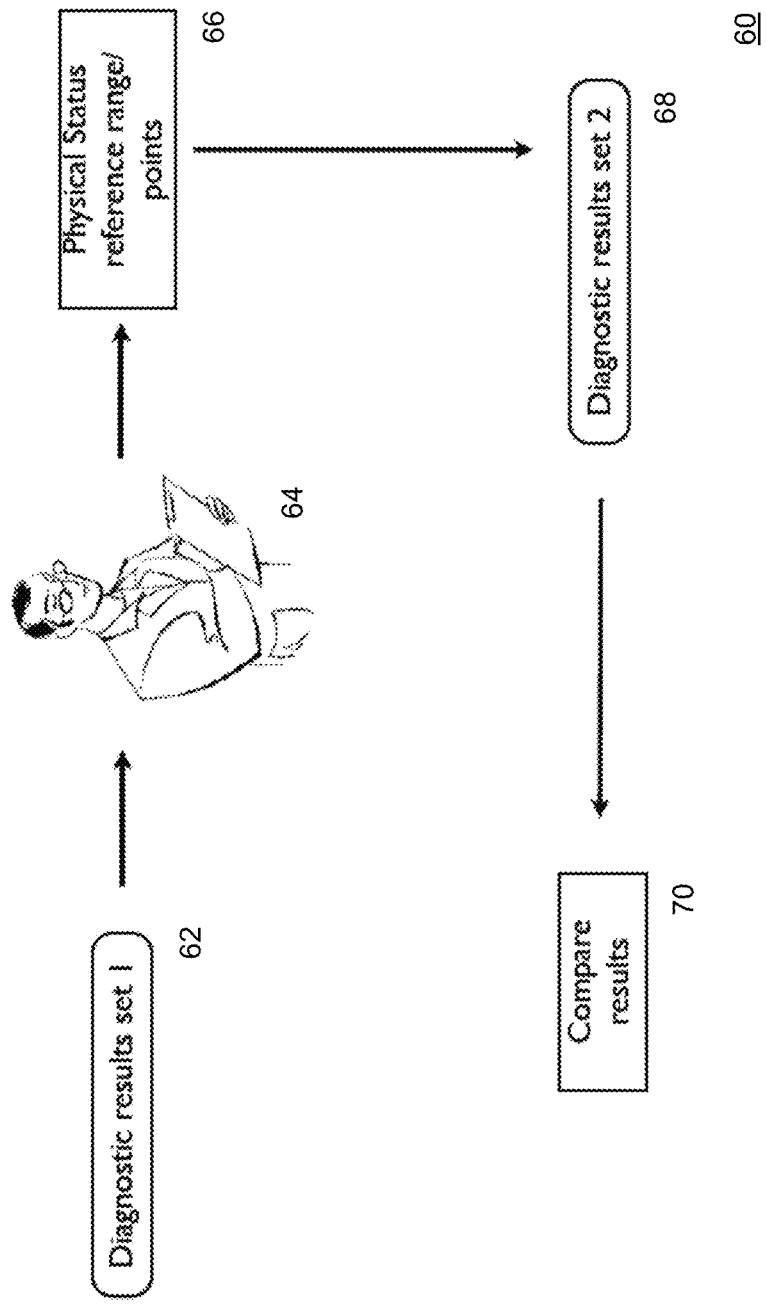
FIG. 7 illustrates a system or environment, and the steps involved in monitoring physical status using a patient-specific reference values, in accordance with an embodiment.

FIG. 7 illustrates a system or environment 60, and the steps involved in monitoring physical status using a patient-specific reference values, in accordance with an embodiment. For example, as shown in FIG. 7, upon generation of a set of diagnostic results 62, a medical professional 64 can note the patient's physical condition, and create a set of reference ranges/points 66. After a period of time or an event, a second set of reference values 68 can be generated, and compared 70 with the first.

Figure 8:
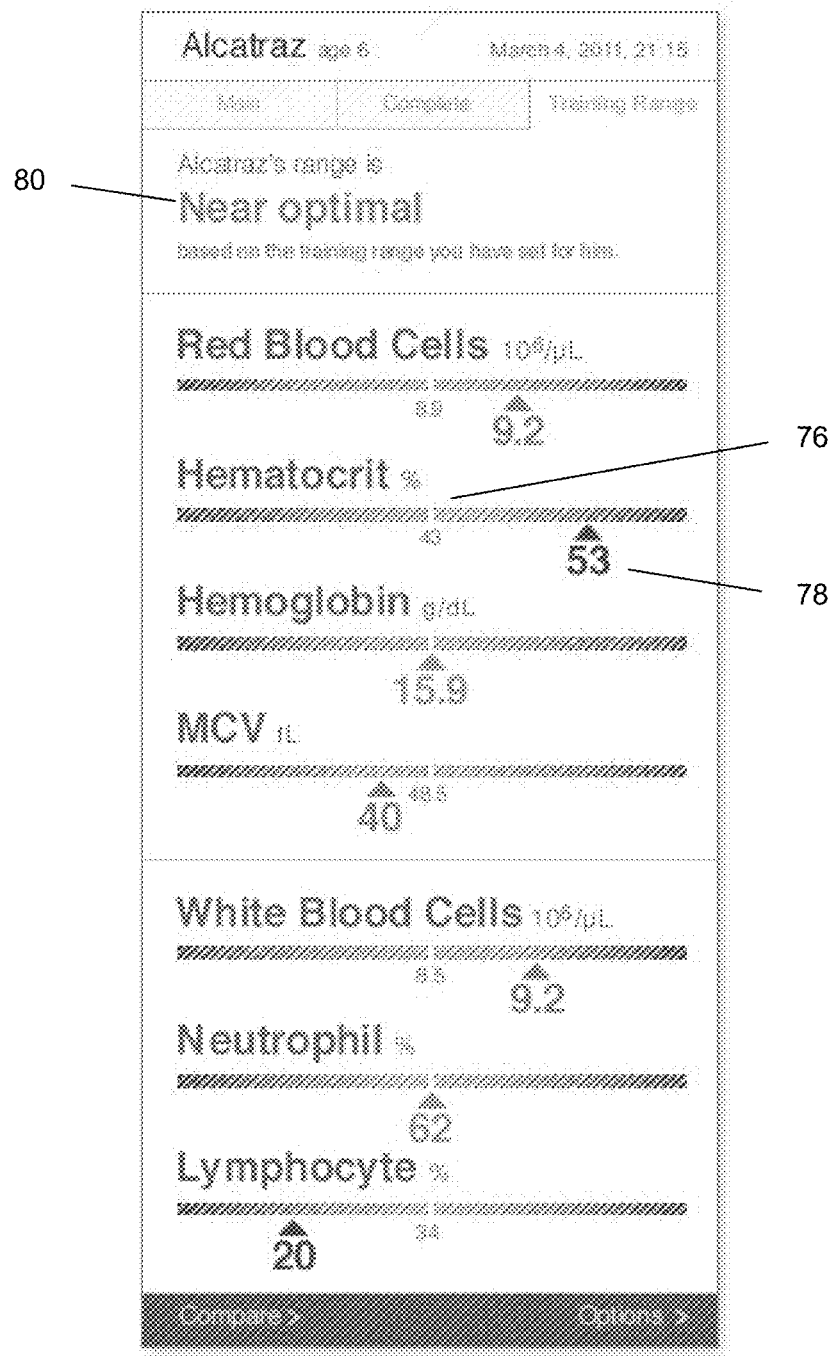
FIG. 8 illustrates an example interface for combining patient blood results with patient-specific information, in accordance with an embodiment.

FIG. 8 illustrates an example interface 74 for combining patient blood results with patient-specific information, in accordance with an embodiment. As shown in FIG. 8, a point can represent a reference point specific to the patient under a certain physical condition. For example, a racehorse in training may have a set of blood results stored by its trainer as its 'optimal training range'. The trainer knows that within this range the horse is displaying peak physical condition. As shown in FIG. 8, a first point (76) can represent the 'optimal' score, while a second point (78) can represent the actual score from the most recent blood result. The header (80) gives an account of the overall context of the results this may or may not be calculated using a set of mathematical algorithm(s) and the standard deviation of current results from the optimal results for a specific physical condition.

Figure 9:
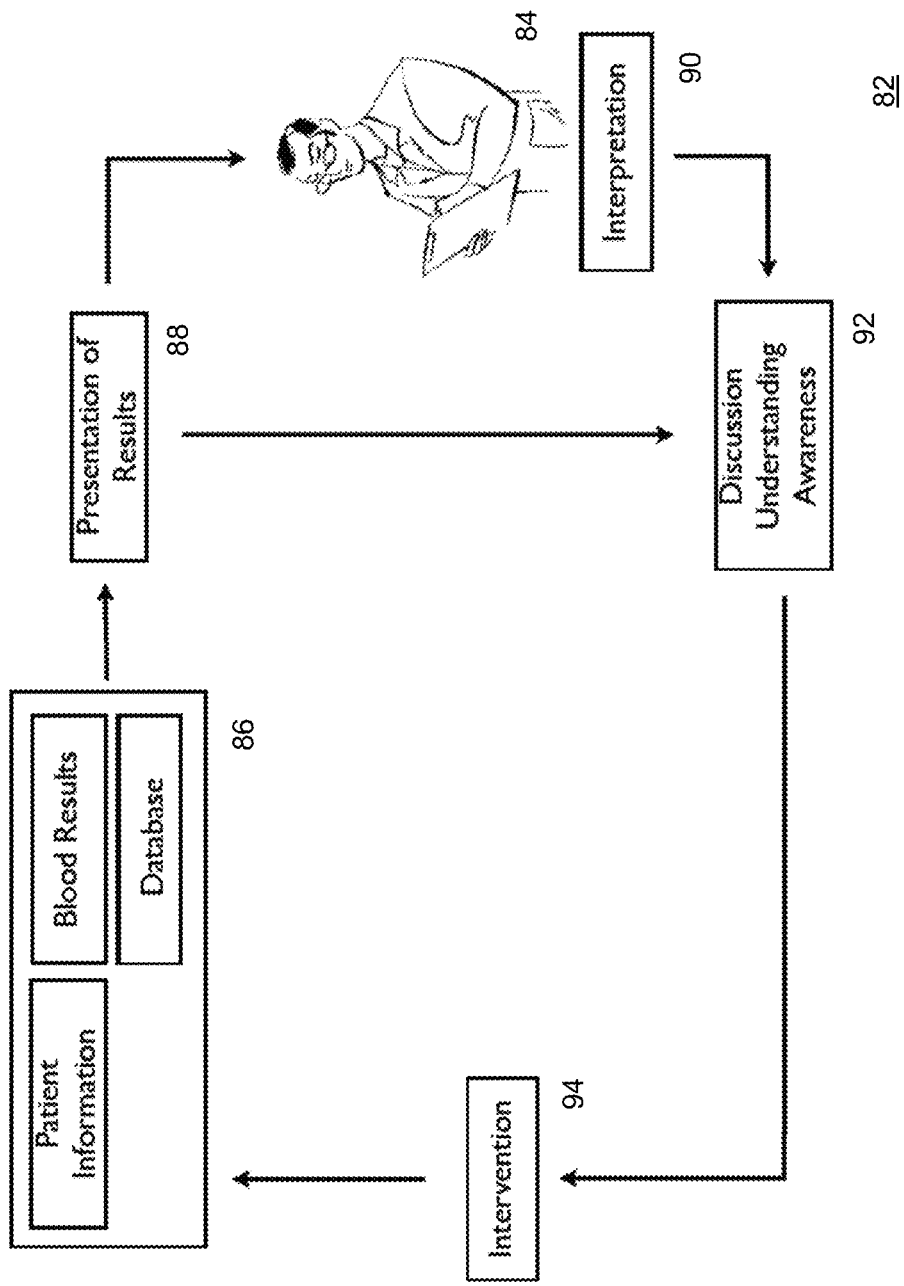
FIG. 9 illustrates the flow of information that may be optionally used in establishing a patient's physical status and the communication of that information to that patient or in the case of animal healthcare, the animal owner/carer, in accordance with an embodiment.

FIG. 9 illustrates the flow of information 82 that may be optionally used in establishing a patient's physical status and the communication of that information to that patient or in the case of animal healthcare, the animal owner/carer, in accordance with an embodiment. As shown in FIG. 9, a medical professional, veterinarian, or other carer 84 (or the subject/patient themselves), can receive patient information 86, such as blood results from a database, and present those results in a readily understandable manner 88, such as using ranges and points as described above. This can allow the carer to make an interpretation or diagnosis 90 and/or provide more meaningful feedback to the subject/patient, or to another medical professional, veterinarian, or other carer 92, to provide a customized and more effective intervention 94 for this subject/patient and their current needs. This flow and clear communication of accurate information may lead to greater understanding and awareness and the use of effective intervention.

Figure 10:
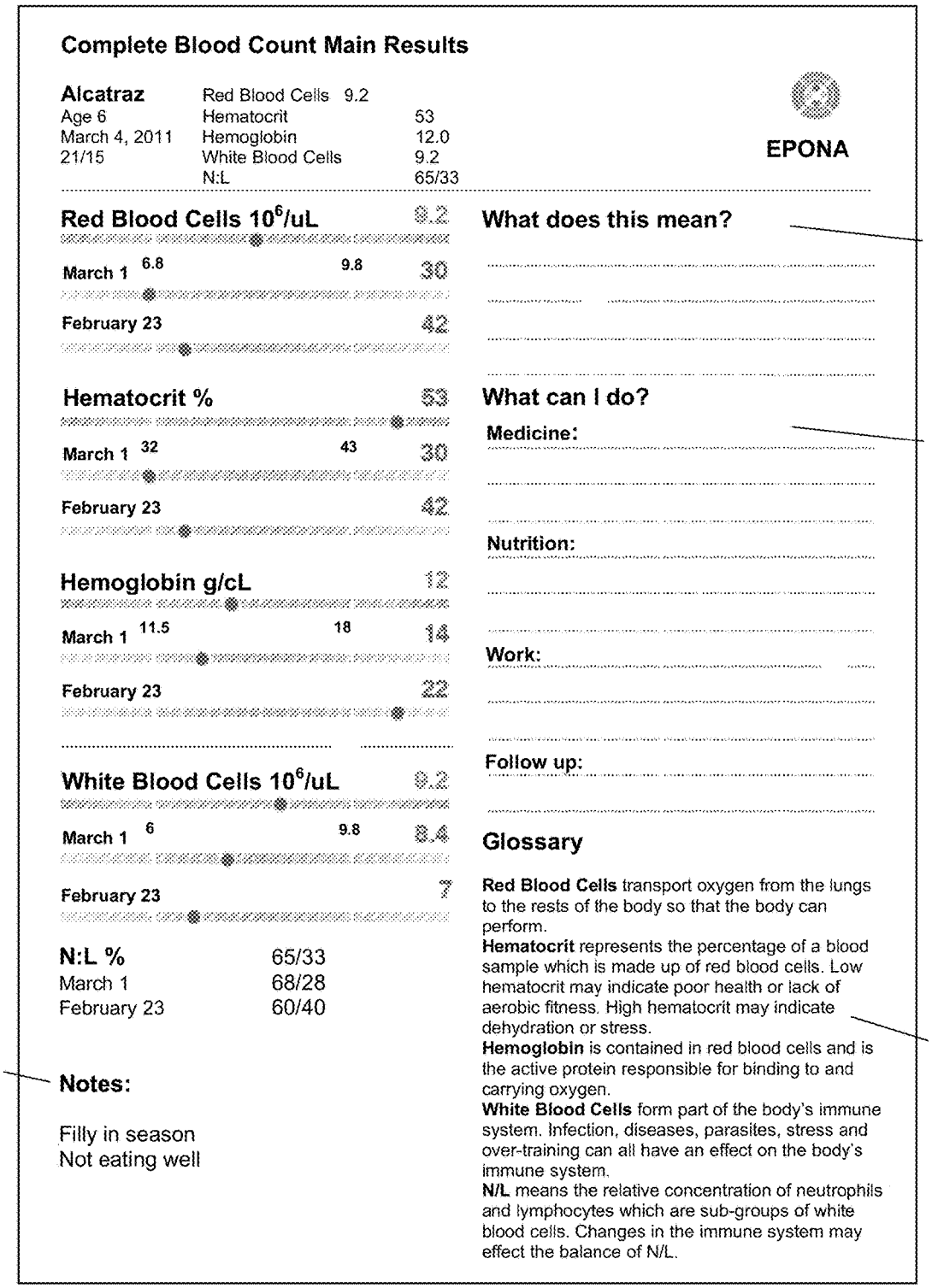
FIG. 10 illustrates an example of a printout design that combines patient blood results with patient-specific information, in accordance with an embodiment.

FIG. 10 illustrates an example of a printout design 98 that combines patient blood results with patient-specific information, in accordance with an embodiment. As shown in FIG. 10, in addition to specific subject/patient information, generic information about the blood result parameters can also be included (100). In accordance with an embodiment, patient-specific notes can be added that are supplemental to the blood results (102). Point 104 illustrates the use of branded and/or trademarked scores that relate to intervention, and may or may not be manually completed by the medical professional. In accordance with some embodiments, information can be presented in a "What can I do?" (105), or similar format, to present possible options and interventions to the user/carer in an easy-to-use manner.

Figure 11:
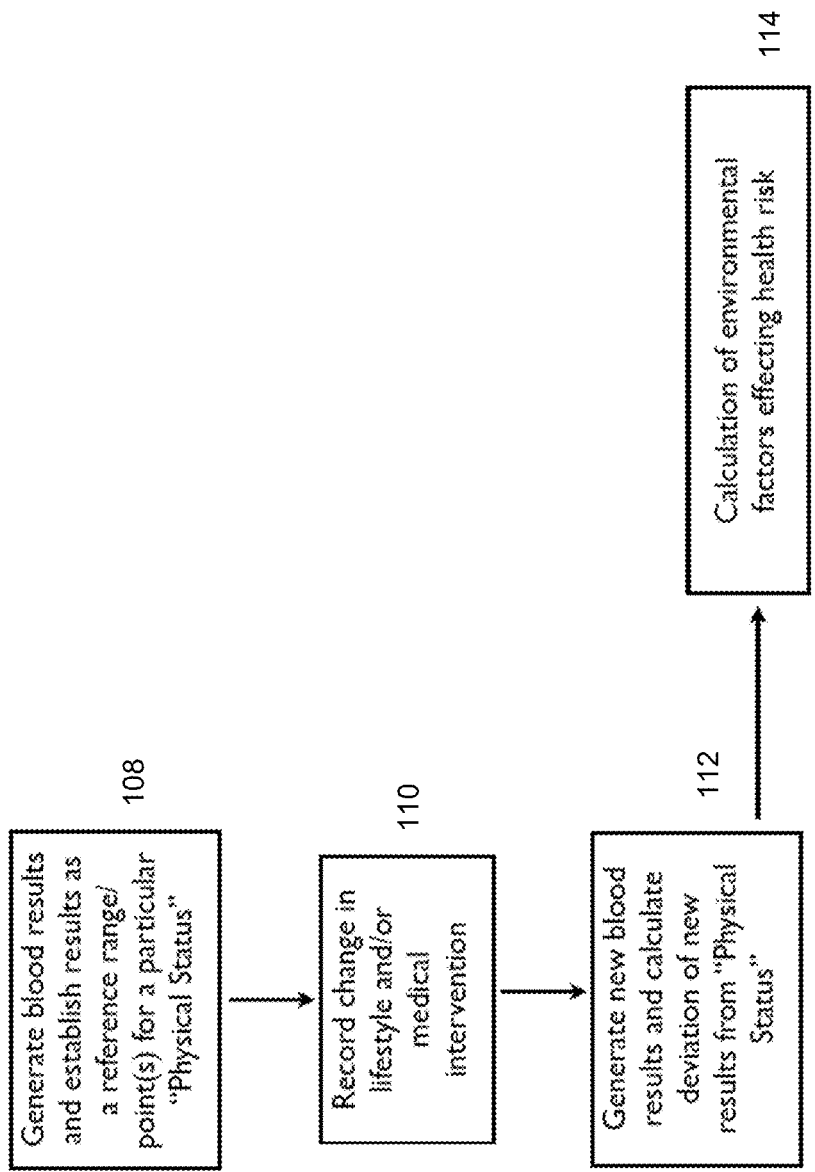
FIG. 11 illustrates the steps involved in assessing the effect of specific interventions on 'Physical Status' reference point/range or set of reference points/ranges, in accordance with an embodiment.

FIG. 11 illustrates the steps involved in assessing the effect of specific interventions on 'Physical Status' reference point/range or set of reference points/ranges, in accordance with an embodiment, together with the use of this comparison to calculate and identify risk factors in the individual patient's health. As shown in FIG. 11, step 108 includes the generation of blood results and establishing the physical status of the patient at the time the results are generated. In accordance with an embodiment the results are then used to establish a reference range, set or reference ranges, a reference point or a set of reference points that represent that Physical Status in that individual patient. Step 110 includes the collection and formation of data and information, for example, the kinds of medical interventions used to treat a patient. Step 112 includes the creation of new blood results and the comparison of these blood results to the established range(s)/point(s) for the Physical Status. In accordance with an embodiment, mathematical algorithms can be optionally used at this stage to calculate the deviation of new results from the established Physical Status. Step 114 includes relating deviations to interventions from step 112. In accordance with various embodiments, the system and the steps described above may be repeatedly used to establish patterns and verify results, which may or may not include use of a machine learning system.

Portable System for Clinical and Performance Evaluation

Figure 12:
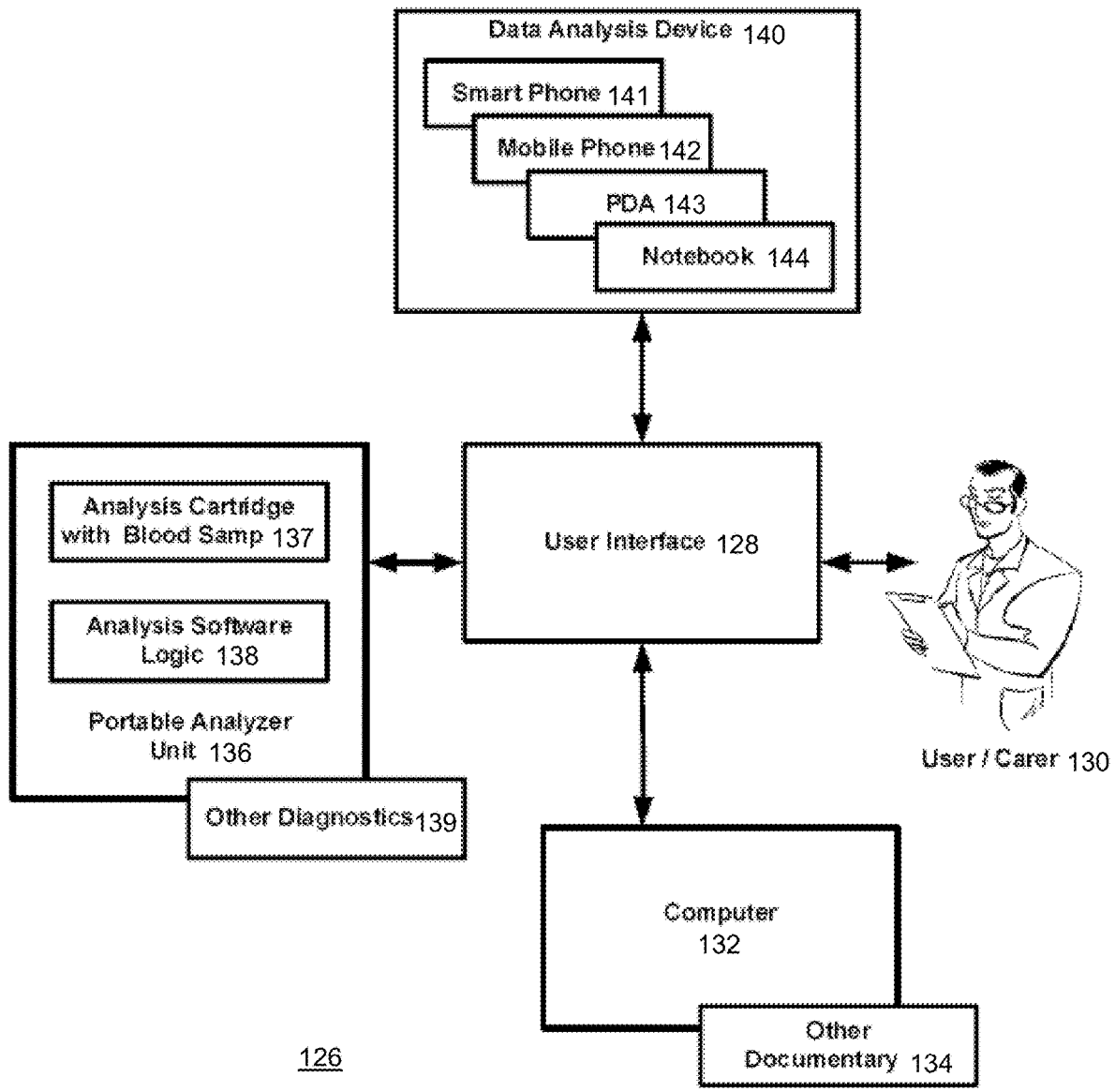
FIG. 12 shows an illustration of a system for clinical and performance evaluation, in accordance with an embodiment.

FIG. 12 shows an illustration of a system 126 for clinical and performance evaluation, in accordance with an embodiment. As shown in FIG. 12, the user or carer 130 can use the user interface 128 together with a portable analyzer unit 136, (an embodiment of which is described in further detail below, and which in some embodiments can include, e.g. means for receiving a blood analysis cartridge 137, an analysis software logic 138, other diagnostics 139 and/or other features), or alternatively with another data analysis device 140, such as a smart phone 141, mobile phone 142, PDA 143, notebook computer 144, or other mobile device, or alternatively a networked, centralized or other computer 132 or other documentary means 134.

Figure 13:
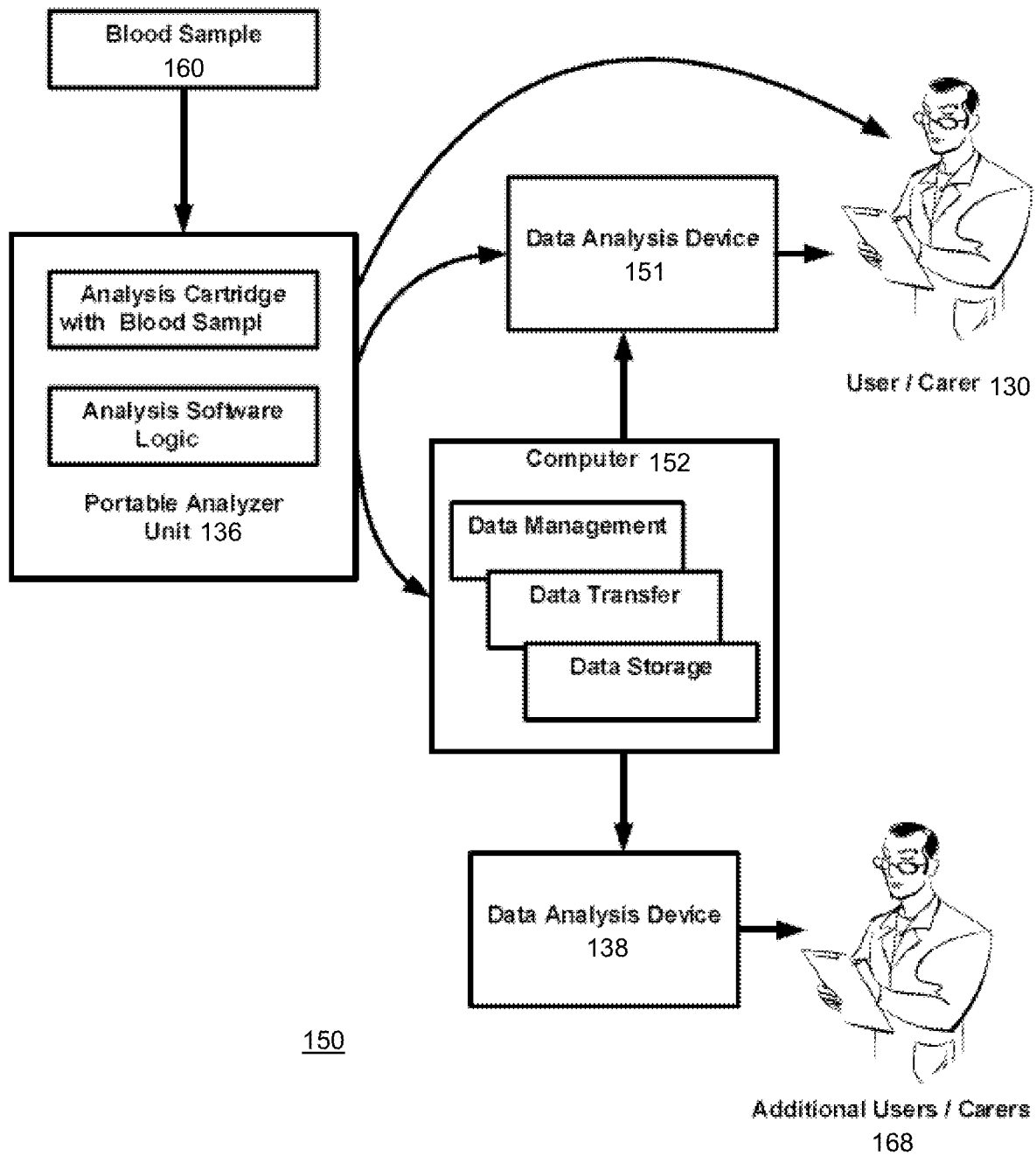
FIG. 13 shows an illustration of a system or environment for sharing clinical and performance evaluation information, in accordance with an embodiment.

FIG. 13 shows an illustration of a system or environment 150 for sharing clinical and performance evaluation information, in accordance with an embodiment. As shown in FIG. 13, signals generated from biological samples, such as blood samples 160, are transformed into quantifiable data that can be readily transmitted between multiple devices in multiple locations, including additional computers 152, data analysis devices 151 and users or carers 168.

This may create significant economic and health benefits. For example, a racehorse trainer who may have horses in training at multiple locations under the supervision of multiple assistant trainers can benefit from real-time and efficient information flow from individual horses to include blood analysis data, and other diagnostic and documentary information, from almost any location. For example, information from animal blood can be validated in real-time at centralized databases, e.g. an online database. The regular screening of blood from animals at multiple rural locations can create information on animal health, stress and immune systems at a centralized location in real-time therefore enabling control centers to pinpoint areas of potential disease outbreak in a rapid and economic manner. Such a system and method may for example, create significant benefits in the prevention of the spread of animal epidemics and in the monitoring of disease in food animals.

Figure 14:
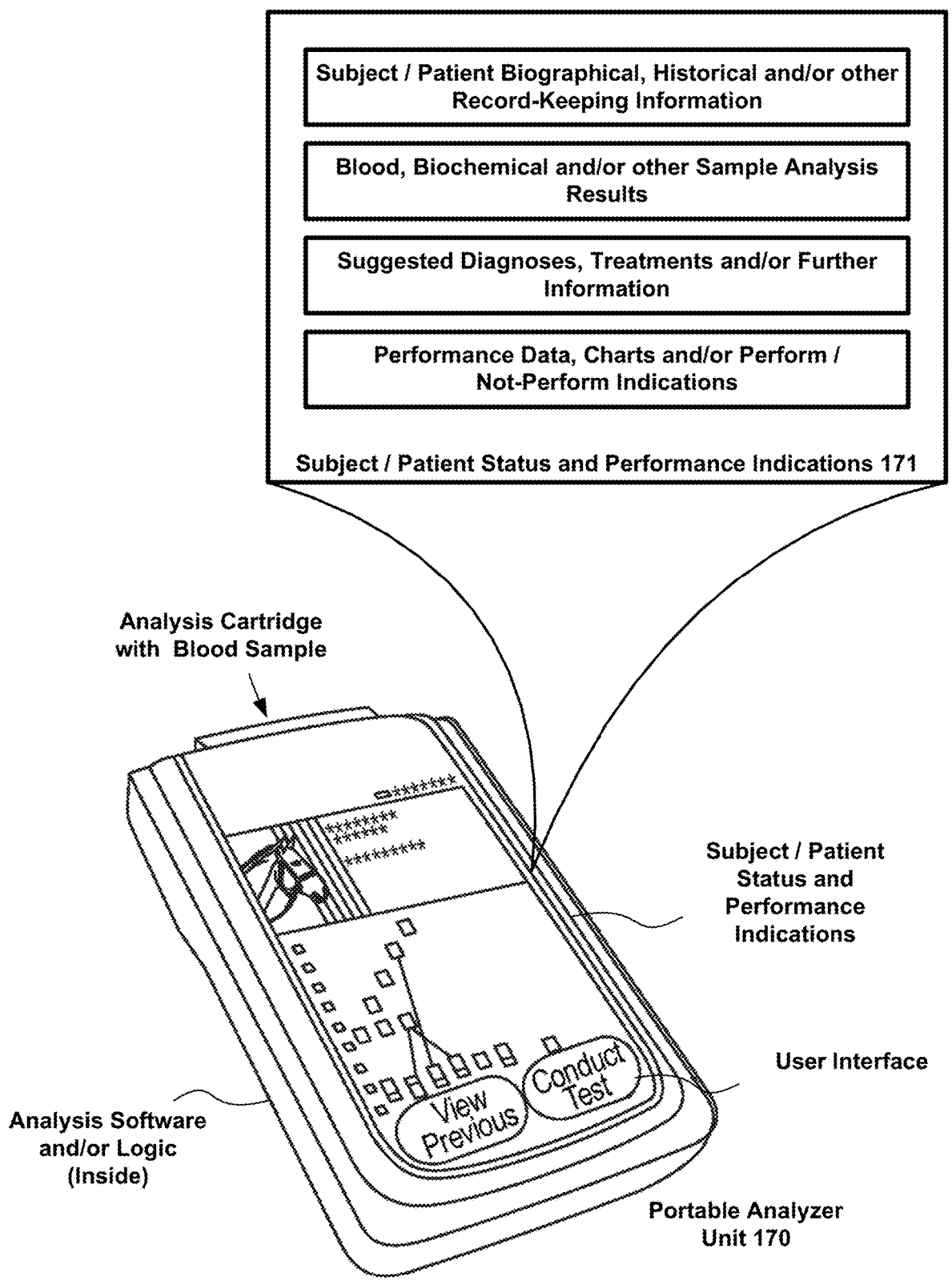
FIG. 14 shows an illustration of a portable analyzer unit that can be used to provide clinical and performance evaluation, in accordance with an embodiment.

FIG. 14 shows an illustration of a portable analyzer unit 170 that can be used to provide clinical and performance evaluation, in accordance with an embodiment. As shown in FIG. 14, the portable analyzer unit can accept an analysis cartridge with a sample, such as a blood sample. For example, in accordance with an embodiment, different types of analysis cartridge can be interchangeably used, for example, a first cartridge to analyze an equine hematologic complete blood count (CBC), or a second cartridge to perform a CBC for another type of animal, or a third cartridge to perform an enzyme, protein or other type of biochemical analysis. The portable analyzer unit further includes an analysis software and/or logic, which can be provided as software and/or firmware or other logic or coding. Depending on the particular implementation, the analysis logic can be provided within the portable analyzer unit itself and/or by the analysis cartridge. Supplemental analysis logic can be added later as necessary, to provide support for new analysis cartridges and tests, or to provide support for new functionality and use cases, such as logic for particular use in bovine border patrol logic, or logic for particular use in thoroughbred racehorse training. A user interface is provided to display subject/patient status and performance indications 171. Depending on the particular implementation, the analysis software logic can be configured differently for different individual patients, animals, or types of animals and different needs, based on a different understanding of those animal type's underlying physiologies and how their performance is related to observational data. For example, an equine-particular logic can be configured to consider such factors as:

- The knowledge that particular characteristics or problems are pertinent to the animal type, for example, in the use case of a thoroughbred horse that such animal types are known to be prone to equine exertional rhabdomyolysis; or that a stressed horse may exhibit temporarily elevated splenetic red blood cell levels.
- Actual blood or other sample analysis information for the current animal, such as its white blood cell and red blood cell counts, as determined by the analysis cartridge; and levels and ratios of analysis information, such as hematocrit or packed cell volume (PCV) levels, that are known to be indicators of health or performance.
- Additional physiological data for the current animal, such as its heart rate or body temperature, which can be determined automatically using additional testing devices, or can be manually input into the device by the carer.
- Additional subjective and/or intuitive information that is pertinent to the intended use case and the current animal, such as in the case of a racehorse whether the horse appears stressed, or whether in the trainer's opinion it appears to be galloping "well" or "better" than the previous day.

This information can be collected and algorithmically used by the system to guide the user in obtaining information from the portable analyzer unit including, for example, providing output of a subject/patient's biographical, historical and/or other record-keeping information; reviewing blood, biochemical and/or other sample analysis results provided by the analysis cartridge; receiving suggested diagnoses, treatments and/or further information related to the health of the animal; and receiving other indications of performance data, charts, or perform/not-perform indications, and other information that may be useful to the user or carer.

In accordance with an embodiment, the user interface may be a cloud computing system that is accessed or interfaced on multiple devices either simultaneously or at different times. Blood analysis data may be automatically uploaded onto the UI. The UI may collect data input at the time of blood analysis. The carer can input additional information, either diagnostic or documentary, in real-time relative to the blood cell count. Therefore, data inputted by the carer has high relevance to the blood cell count and can build on the diagnostic outcome leading to an improved outcome of referral or intervention. In addition the UI can be used to characterize particular individual animals. For example, a horse may be recorded as having a particular response to training where an intense training session has been noted to reduce the red blood cell count and elevate certain white blood cell counts. By recording training intensities along with blood analysis data the trainer can review how particular training practices may affect individual horses and thus use the system to enable optimum performance and returns from his/her animals. Alternatively, a horse may have been noted to be in particular good form when its blood cell numbers were recorded to be in a specific region. This may give the trainer a "goalpost" to aim for when the next race is coming up. Racehorse trainers have been noted to call this scenario "the perfect blood picture".

Figure 15:
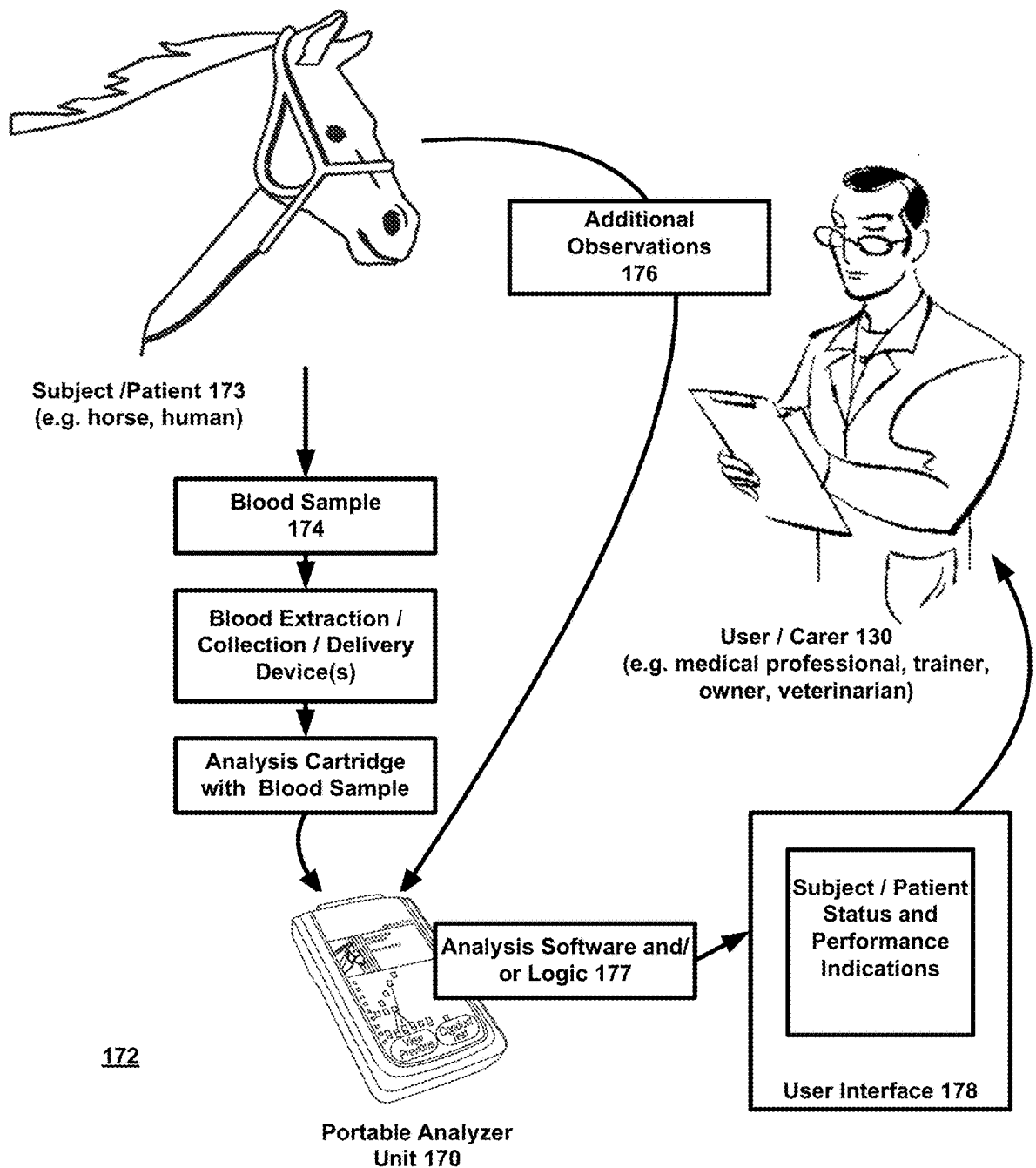
FIG. 15 shows an illustration of a portable analyzer unit being used to provide clinical and performance evaluation, in accordance with an embodiment.

FIG. 15 shows an illustration of a portable analyzer unit being used to provide clinical and performance evaluation 172, in accordance with an embodiment. As shown in FIG. 15, the process can be used with a subject/patient 173, such as a horse or other human or non-human animal, by a user or carer 130, such as a medical professional, trainer, owner, veterinarian, or other user. A blood sample 174 is extracted from the subject/patient, using one or more blood extraction, collection, or delivery devices, and is placed within the analysis cartridge which is then placed into the portable analyzer unit. The user can also input additional observations 176 about the subject/patient into the portable analyzer unit. As described above, analysis software logic 177 then uses the information from the analysis cartridge, together with data from the additional observations, to provide an immediate output to the user via a user interface 178, which can include information about the subject's current health, status and performance indications.

Performance Potential Scoring System

FIGS. 16-19 show illustrations of how the system can be used to provide a performance potential score, in accordance with an embodiment. In accordance with an embodiment, the system and method can be used to create a score to estimate performance potential, including an amalgamation of various diagnostic and other relevant information, and converting it algorithmically to a score which may be representative of performance potential. In accordance with an embodiment, the system can be provided as a machine learning system that learns from collecting diagnostic and other information and data recorded at a certain time point, and relating it to performance measurements and other information and data taken at a separate time point. This system is particularly useful for assessing immediate or real-time performance potential of individual animals, such as sporthorses.

In accordance with an embodiment, the system includes a point of use device or multiple devices, such as a portable analyzer unit as described above, or a computational device and cloud based computing system capable of collecting and amalgamating data from a particular location and at a particular time point.

In accordance with an embodiment, the point of use device(s) can collect data relevant to biological samples. In addition, the point of use device(s) may be capable of further diagnostic analysis, from blood, milk, urine or otherwise, or can be used in conjunction with other diagnostic equipment and devices. Other analysis may or may not commonly include enzyme analysis, electrolyte analysis, protein analysis, lactic acid analysis and any other relevant biological sample diagnostic analysis and information. In addition to biological sample diagnostic analysis, other diagnostic and documentary information may be measured and recorded. For example, temperature, heart rate, respiration rate, respiration volume, VO2Max, lactate threshold, animal weight, information related to sleep, lap times, split times, speed, distance, geographical positioning system (GPS) data, ground conditions, jockey information, carer personal opinion input and other relevant diagnostic and documentary information.

In accordance with an embodiment, the system and method uses algorithms to transform biological sample diagnostic, and other relevant information, into a score that estimates or predicts immediate performance potential at the animal's side. The system can be provided as a machine learning system, which uses diagnostic information generated at a particular time point, prior to performance, and relates it to the outcome of that performance by documentary and diagnostic measurements carried out in-and-around the performance. Over time and with use, the system can be used to generate accurate information for predicting performance potential. The system, by its nature, can become more accurately aligned with predicting performance potential scores over time and through use. This system may "self-generate" in a manner that can be recognized by the user, while the user collects diagnostic and other information on a regular basis using a portable device, or other suitable device. The system can also be provided as a machine learning system that is particularly useful for use with a portable device.

For example, in a usage scenario, a racehorse may have blood diagnostic, as well as other diagnostic measurements taken the morning of an intense training session. At approximately 6:59 am, all of the information may be generated and amalgamated in a database. At 7:00 am the database may generate a 'dataset' of scores specific to the individual. Each score may or may not be representative of performance potential. Subsequently, at 10:00 am the horse may then be put through an intense training session. Performance measurements may be recorded at the time or in-and-around the time of the training session. Such measurements can be used to generate a score representative of the outcome of the horse's performance. Such performance-measurement score can also be generated using a constant algorithm, so that variables in calculation are minimized. The machine learning system can then relate the performance-measurement score from 10:00 am to the dataset of scores generated earlier that morning at 7:00 am. Machine learning artificial intelligence may then be used to identify which particular scores in the dataset relate to performance, and to what extent they each contribute. Furthermore, this system may be used to design and develop novel algorithms for predicting performance based on the scores in the dataset. Over time, this system and method for machine learning, can single out algorithms that create accurate performance-potential indicating scores for that individual horse. These scores can be generated at the patient/subject's side using a portable device for biological sample analysis.

In accordance with an embodiment, the machine learning system can be configured to be either sensitive, or not sensitive, to the user and their characteristic data input. For example, other documentary information may include a YourScore™ system and method for information input. As described herein, YourScore™ is a system and method for rapid and easy collection of documentary input from the user. This system can score any parameter that the carer feels is relevant to the animal's performance. For example, a racehorse trainer may record their opinion on an individual horse's performance directly after a race or intense training session. Such record may include information on the horse's respiration rate, recovery time, distance ran, lap time, or any other information that the trainer feels is relevant. Data input can take the form of a survey, slider-bar system, typed input, SMS message, audio, visual or other suitable data input or collection system. YourScore™ may also be used at any other time or location to record information from the user for example, pre-performance information. Combining YourScore™, user log-in, animal identification and machine learning, this system and method can quickly and accurately learn the overall patterns used by individual trainers and identify when a particular user is prone to over-scoring or under-scoring, or indeed to over-scoring or under-scoring with respect to a particular individual animal.

In accordance with an embodiment, the machine learning system described herein can incorporate a system to identify patterns that are characteristic of individual animals. For example, a horse that is prone to equine exertional rhabdomyolysis (EER) may typically experience characteristic diagnostic and other patterns or triggers in the onset of an episode of EER. Such patterns or triggers may be identified by the artificial intelligence machine learning system associated with the cloud computing database, or other suitable system, that may alert the carer when such patterns or triggers are detected.

As disclosed herein, all such machine learning systems and methods may or may not be included as part of the overall system and method that creates a score to estimate performance potential.

Figure 16:
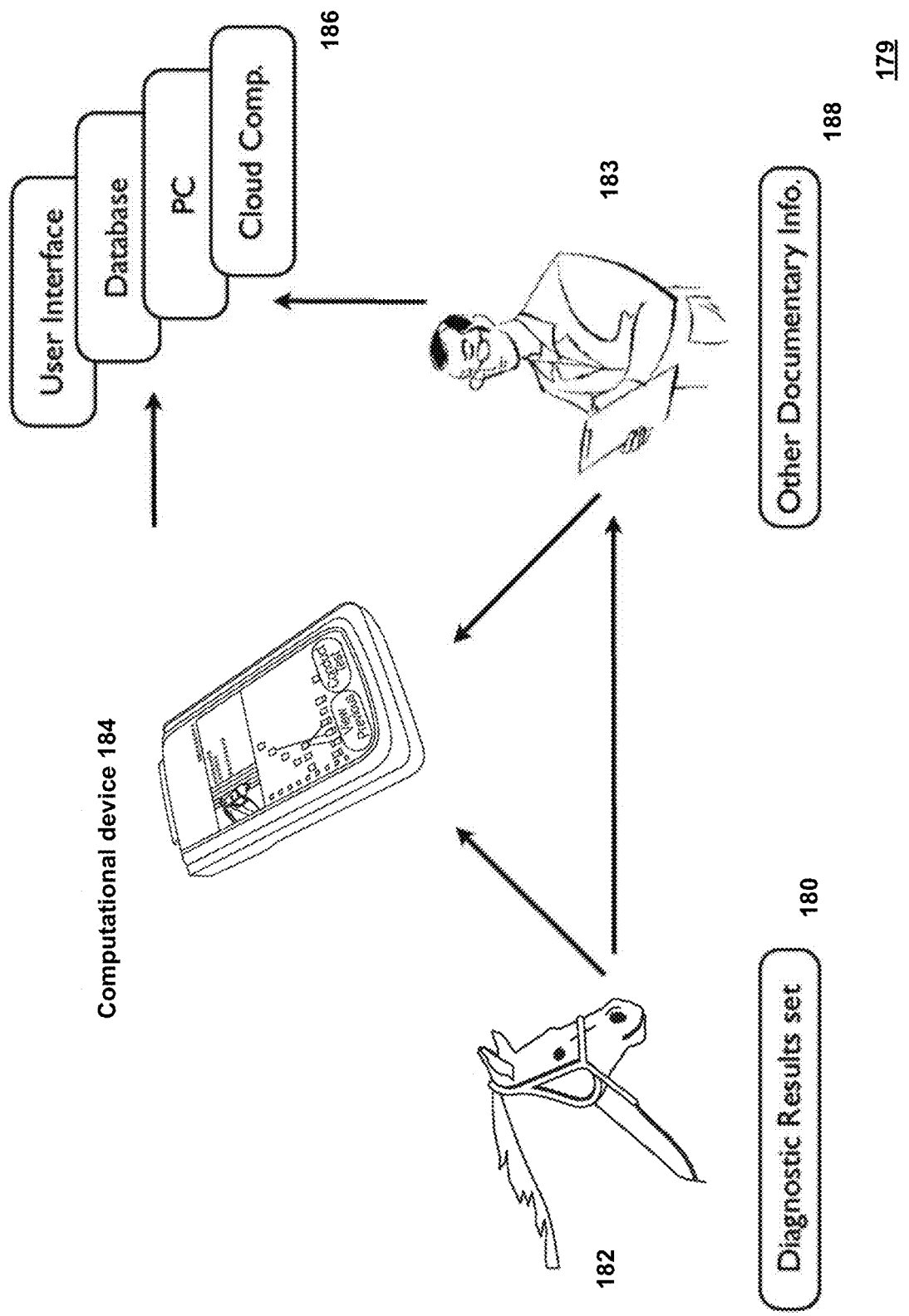
FIG. 16 illustrates a system or environment that allows the collection and amalgamation of data at the subject's side, in accordance with an embodiment.

FIG. 16 illustrates a system or environment 179 that allows the collection and amalgamation of data at the subject's side, in accordance with an embodiment. As shown in FIG. 16, diagnostic information 180 generated from the subject/patient 182, which may include data generated from blood cells, other blood measurements, other diagnostic information such as temperature, heart rate, weight, sleep-related data, performance measurements such as VO2Max, lactate threshold, speed, distance and any other relevant data can be collected and amalgamated by a point of use device such as a portable blood analyzer, smartphone or other suitable device 184. Alternatively, multiple devices 186 used at the subject/patient's side can transmit information to a personal computer, cloud computing system, database, or other centralized data amalgamation point. In addition, other documentary information 188 may be collected and inputted by the carer 183 such as personal notes, audio, video, or other relevant information.

Such collection of data can happen in real-time at the animal's side and link or sync to other wireless or other systems to collect further data, either historical or real-time. All such information may be amalgamated on a single device, multiple devices, user interface, personal computer, cloud computing system, database, or other suitable system.

Figure 17:
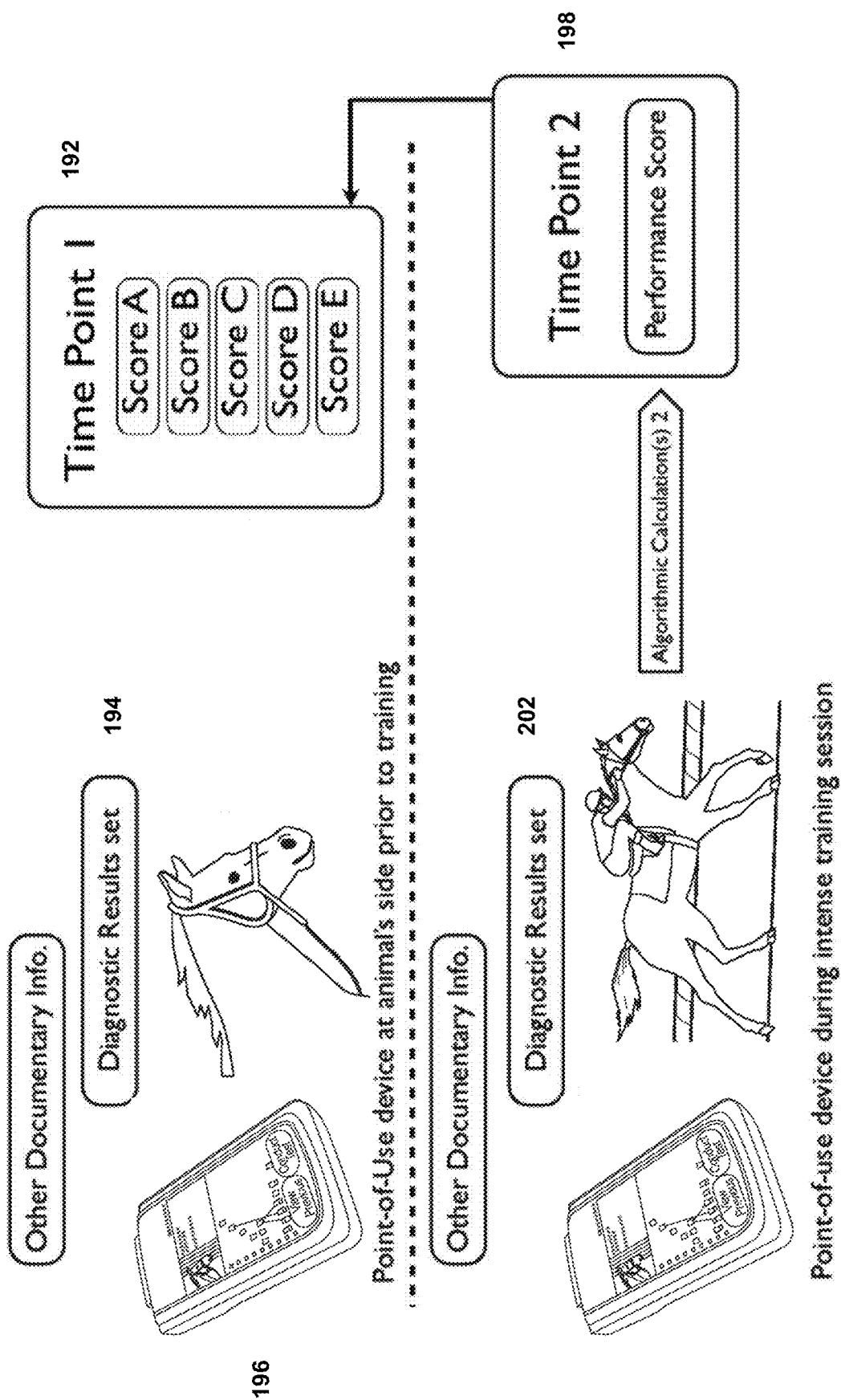
FIG. 17 illustrates a system or environment which incorporates a machine or device to generate accurate scoring for assessing and/or predicting immediate performance potential, in accordance with an embodiment.

FIG. 17 illustrates a system or environment which incorporates a machine to generate accurate scoring for assessing and/or predicting immediate performance potential, in accordance with an embodiment. Prior to time-point 1 (192), diagnostic and documentary information 194 are recorded using a point of use device, multiple point of use devices or other suitable device(s) 196. At timepoint 1 a dataset of scores can then be amalgamated using a computational device such as a smart phone, cloud computing system, database or other suitable system. Subsequent to time-point 1, but prior to time-point 2 (198) a set of diagnostic data 202 may be recorded in-and-around an intense training session or performance. In addition, a set of documentary data may also be recorded. At time-point 2 these results and data may be amalgamated and transformed into a score representative of performance measurements or actual performance achieved. Such score(s) to be generated algorithmically. A comparison of actual performance measurement score(s) from time point 2, to the dataset of scores generated at time point 1 is then carried out. This comparison can be carried out by embedded systems on the point of use device(s), the user interface, personal computer, cloud computing system, database or other suitable system. The system can then use machine learning whereby the score(s) from time point 1 that correlate with most accuracy to the score(s) from time point 2, may be noted, recorded and stored. Over time, and with use, the system can be used to determine which scores or dataset of scores accurately represent or predict immediate performance potential.

Figure 18:
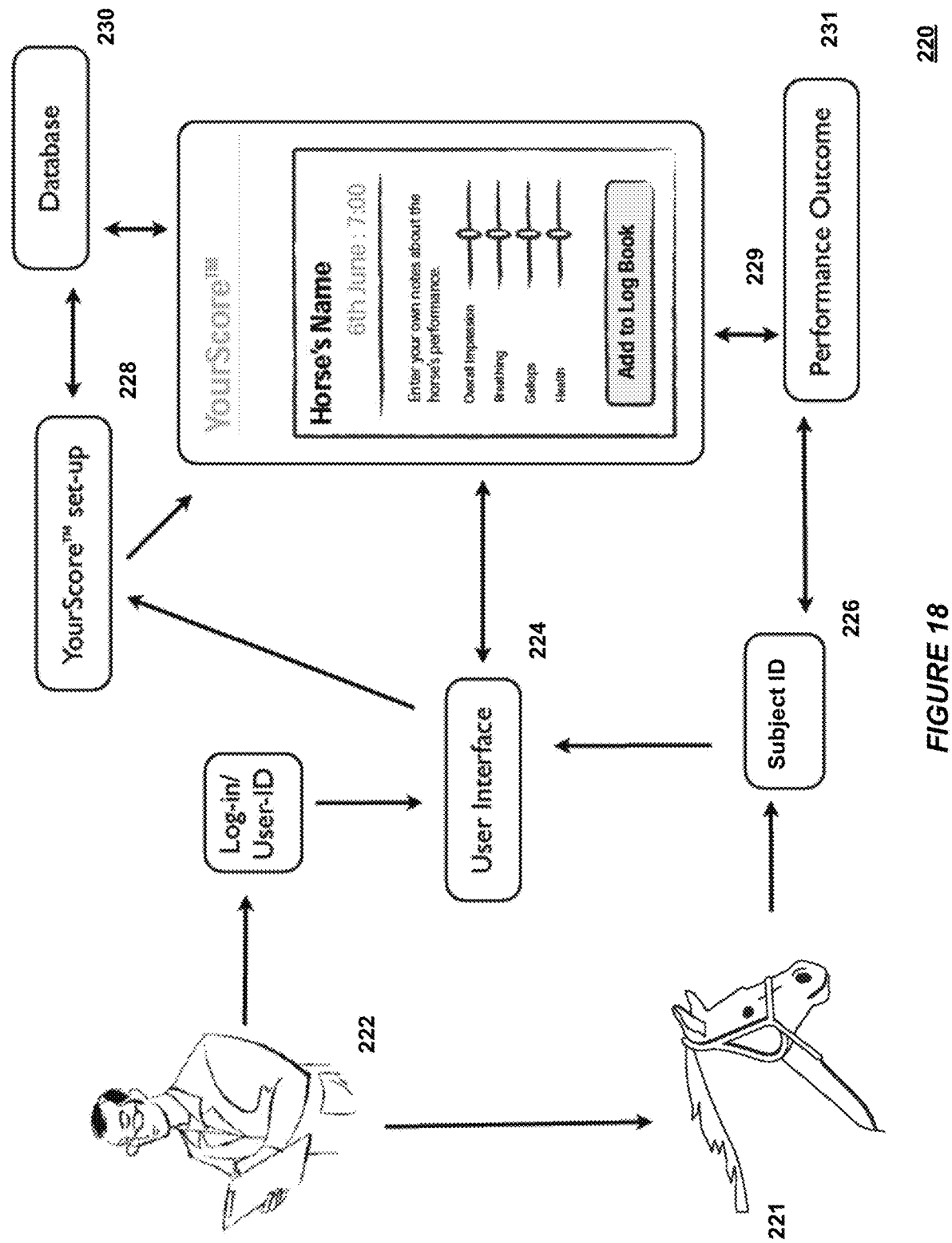
FIG. 18 illustrates a system or environment which provides a combination of YourScore™, user log-in, and subject/patient identification in a system and method for machine learning, in accordance with an embodiment.

FIG. 18 illustrates a system or environment 220 which provides a combination of YourScore™, user log-in, and subject/patient identification in a system and method for machine learning, in accordance with an embodiment. Such system and method includes a user interface (UI) 224 that identifies and collects information from individual users 222 and subjects/patients 221 over time and learns from identifying patterns that re-occur. In addition, depending on the embodiment, users may (or may not) have the option to include a personal set-up feature 228 for the YourScore™ system and method. YourScore™ information 229 associated with individual users can be transferred to a database 230 where information and data can be stored from many individual users. Such information and database can be used to create a system for normalizing scores generated by individual users. Furthermore, subject/patient identification 226 can link YourScore™ to performance outcome scores 231. Such feedback system and method can be used to normalize YourScore™ recordings from individual users relating to individual subjects/patients.

Figure 19:
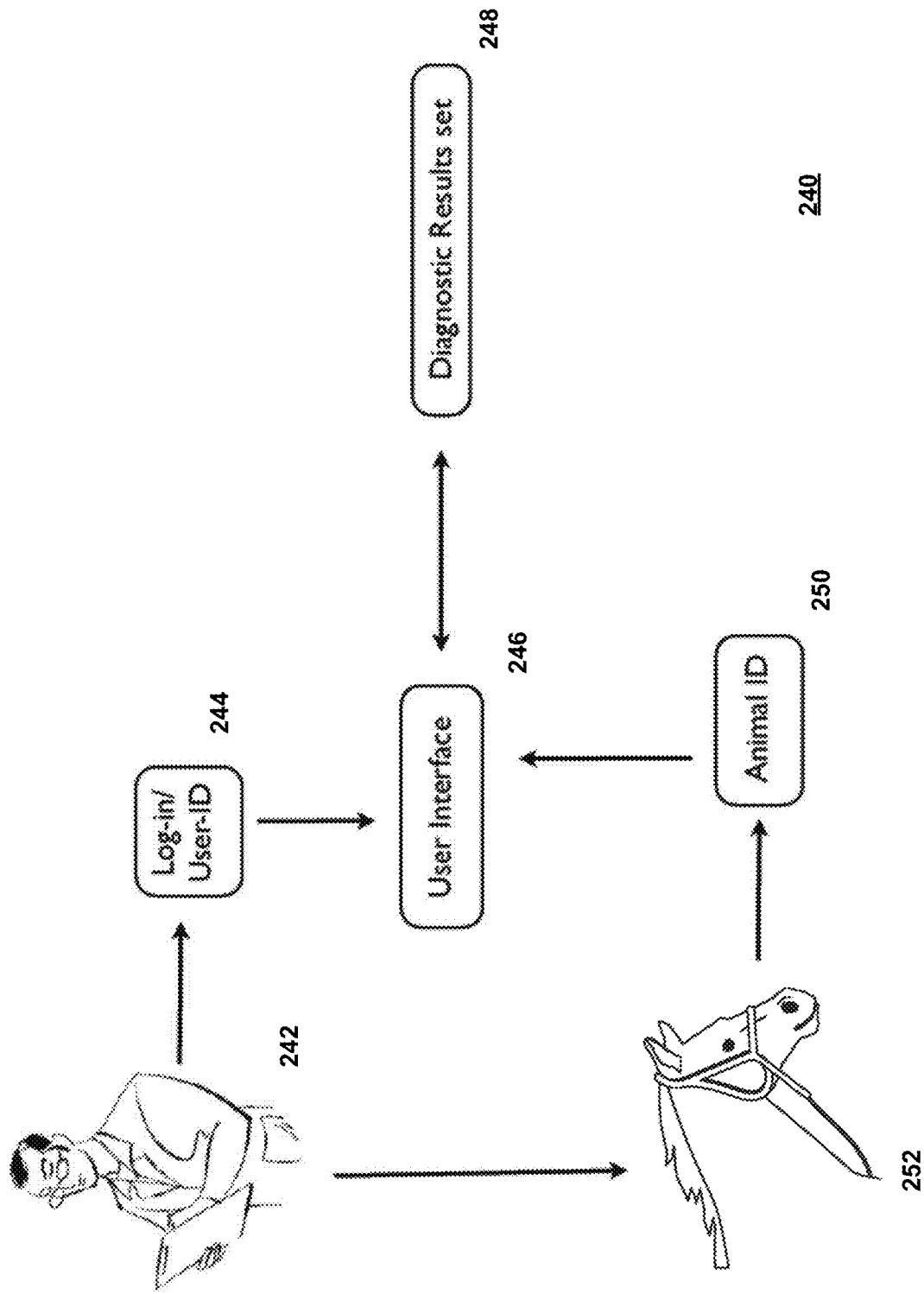
FIG. 19 illustrates a system or environment which provides a combination of diagnostic results, user log-in, and subject/patient identification in a system and method for machine learning, in accordance with an embodiment.

FIG. 19 illustrates a system or environment 240 which provides a combination of diagnostic results 248, user log-in 244, and subject/patient identification 250 in a system and method for machine learning, in accordance with an embodiment. Such system and method includes a user interface (UI) 246 that collects information from individual users 242 and subjects/patients 252 over time, and then learns from identifying patterns that re-occur.

Machine Learning for Optimizing Interventions

Figure 20:
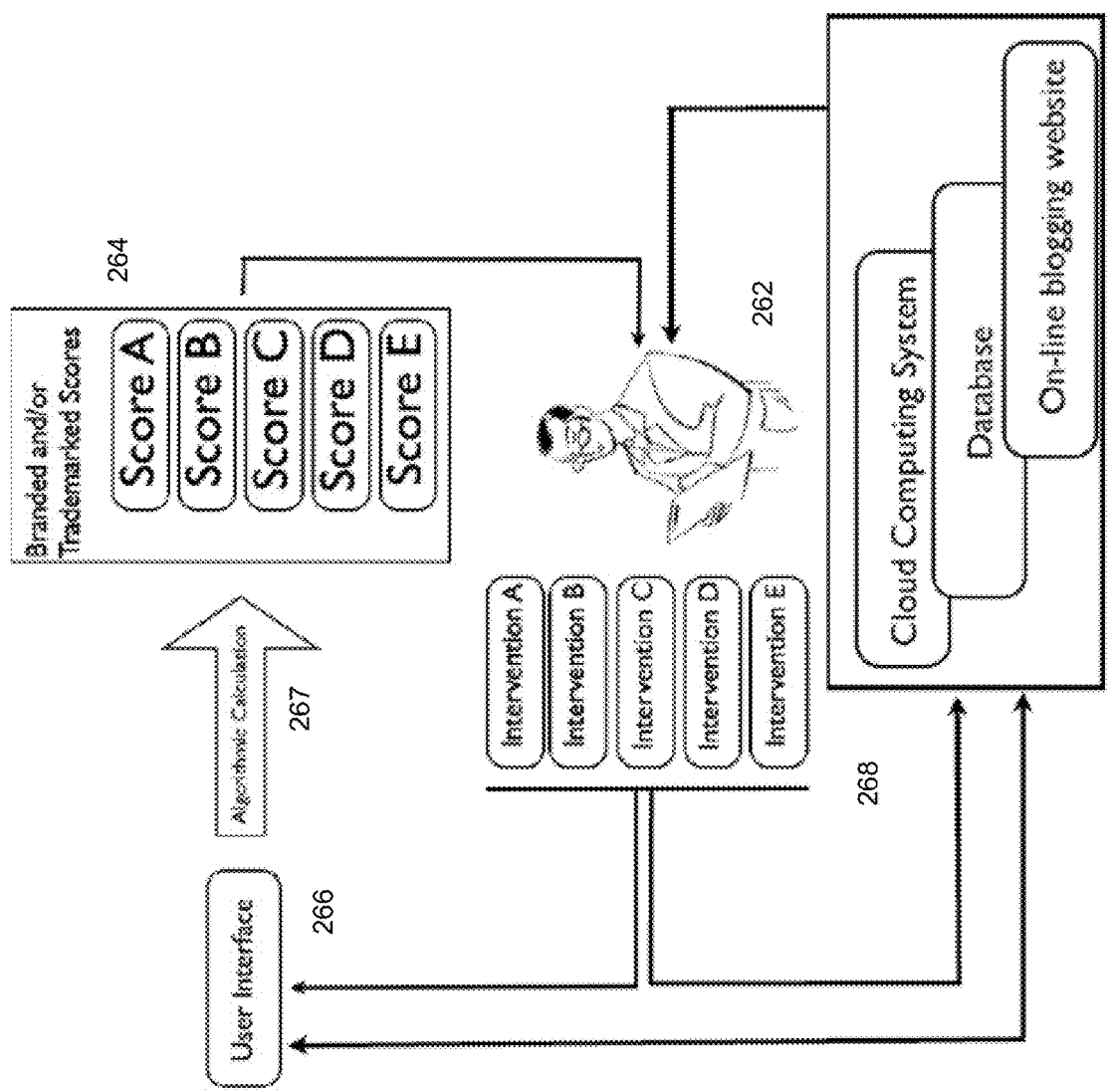
FIG. 20 illustrates a system or environment which supports the use of a user interface embedded on a computational device(s) software application, branded and/or trademarked scores, intervention strategies, and a cloud computing system with online data base in accordance with an embodiment.
Figure 21:
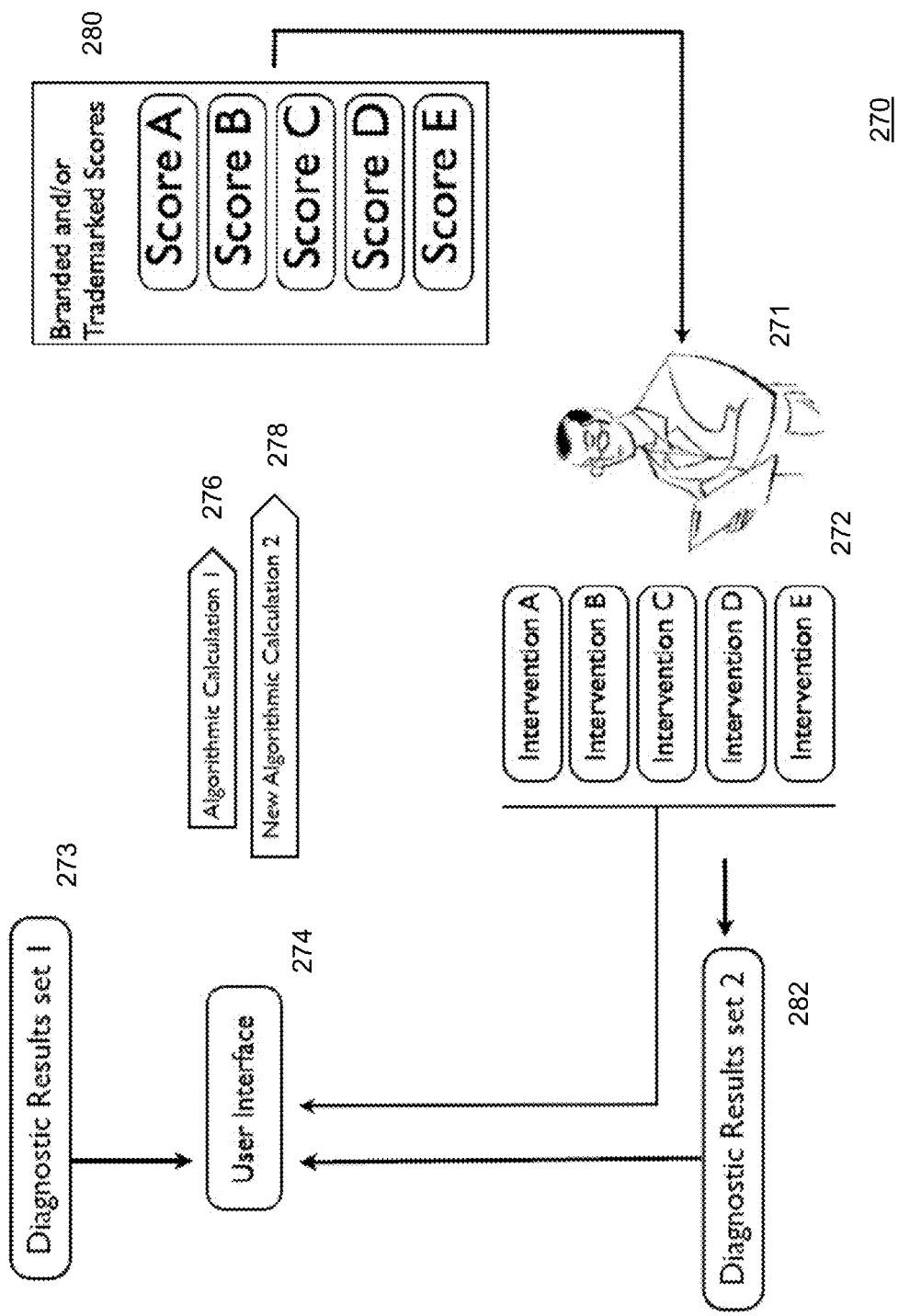
FIG. 21 illustrates a machine learning system or environment, in accordance with an embodiment.
Figure 22:
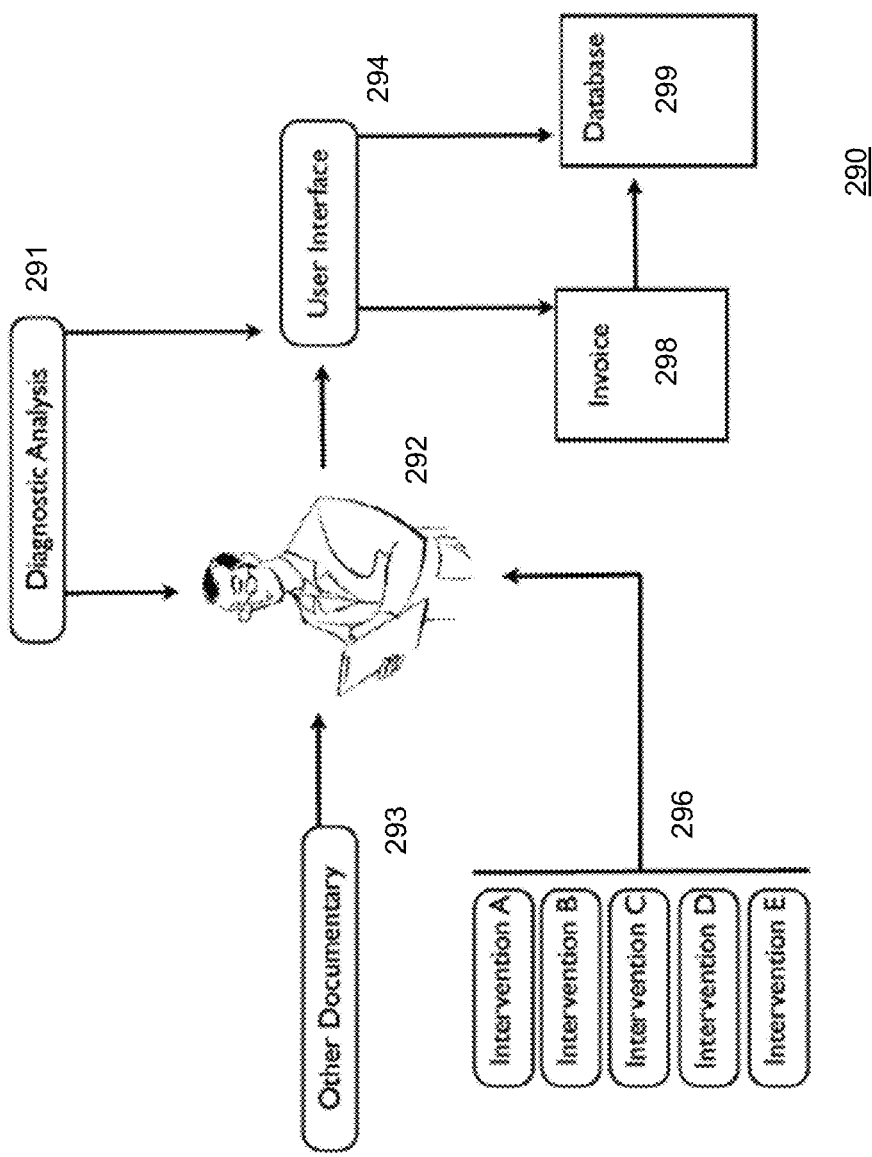
FIG. 22 illustrates an automatic invoicing and information collection system or environment, in accordance with an embodiment.

FIGS. 20-22 show illustrations of how the system can be used to provide machine learning to optimize interventions, in accordance with an embodiment. In accordance with an embodiment, the system can be used to relate biological sample diagnostic information, performance results, and other diagnostic and documentary information to common intervention strategies. Diagnostic information which can include, for example, information from biological samples or tissues, or other relevant diagnostic or documentary information can be inputted through the user interface (UI) via a computational device such as a smart device, or another suitable system, and algorithmically converted (either on the smart device or on a cloud computing system) into a dataset of easy to read scores, such scores may be branded and/or trademarked. These scores should relate, as closely as possible, to common intervention strategies, to help the user decide quickly and clearly which intervention strategy to carry out.

In accordance with an embodiment, the scores are not used to recommend an intervention, but can be linked to websites or databases which provide information on the common interventions carried out by other users, for example, "our information tells us that 100 other users have found that resting the animal over a 5 day period has led to the improvement of this score". Such information can be provided by or generated through a cloud computing system or database which is linked to many users and devices. Similarly, on-line blogs by industry leaders, such as specialist veterinarians or other suitable individuals or group of individuals, can be used to create information sources for users wishing to intervene in the appropriate manner on these branded or trademarked scores.

In accordance with an embodiment, intervention strategies actually carried out by the user can also be inputted into the computational device, so that the data is recorded and stored. For example, this can take the form of a survey, typed input, audio, visual or other suitable method and such information can be stored on a software application, cloud database or other suitable system.

In accordance with an embodiment, the system can include or be provided as a machine learning system, which is implemented or configured to continually improve the sensitivity of the scores, in such a manner so that, over time, the scores consistently become more and more accurately aligned with the outcome of the intervention strategies recorded. For example, the system may recognize that a branded and/or trademarked score that is algorithmically generated from packed cell volume (PCV) and resting heart rate in racehorses, and is related to the intervention of food additives and nutraceuticals, and then may, by use over time, further recognize that administration of nutraceuticals also increases equine mean corpuscular volume (MCV). The system can then incorporate PCV, resting heart rate and MCV into the branded and/or trademarked score. Therefore, over time and use, the system can provide scores that allow the users to see more rapidly and clearly the effect, or lack thereof, of the intervention strategy that they have chosen for any individual animal or group of animals. This machine learning feature can be programmed for an individual user or group of users over one portable analyzer unit or many independent portable analyzer units or other suitable systems, such as for example, a personal computer or smartphone.

In accordance with an embodiment, the machine learning system can be programmed to individual users and individual animals or large groups of users and groups of animals. Identification of users can be provided through password or other suitable user log-in system. Identification of individual animals may occur through radio frequency identification (RFID) microchip scanning, manual input or other suitable identification system. Such technology can be incorporated into the portable analyzer unit, or in separate computational devices such as smartphones, tablet computers or personal computers.

In accordance with an embodiment, the system can be used for recording common interventions carried out for an individual animal or group of animals by individual users or groups of users. Such information can be stored on a portable device, a cloud computing system, database, or other suitable system.

In accordance with an embodiment, the system can also allow for features such as automatic invoicing. For example, costs associated with particular diagnostic analysis and interventions can be inputted and stored on a portable analyzer, personal computer, cloud computing system, database or other suitable system or device. When an individual animal or group of animals associated with an invoice have diagnostic analysis or interventions carried out with them, the costs for those items can be automatically added to the invoicing system. For example, in a racehorse training stables, a trainer may identify an individual horse by RFID scanning of the horse's microchip, manual input or other suitable system. Diagnostic information can then be collected for that horse, for example, complete blood count (CBC) analysis, resting heart rate, temperature, weight, nasopharyngeal endoscopy examination or other relevant information. The trainer may then decide to intervene, for example, by administration of a nutraceutical or other suitable intervention, if any. All of this information can be collected through the UI on a portable analyzer, or other suitable system, and held in the portable analyzer and/or forwarded to the cloud computing system, database or other suitable system.

For each item listed in the example above an associated cost can be added to the invoice for the owner of that horse. If that owner owns more horses in that trainer's stable, all of the costs from the different horses can be added to the invoice for that owner. The system may also be applicable for example, to veterinarians working on behalf of a client or group of clients. The system also gives the user the opportunity to produce itemized billing, giving customers detailed information on all of the items that are included in the bill.

In accordance with an embodiment, the system can collect information from animal healthcare including diagnostic information which may include a biological sample analysis or other veterinary information, documentary information, intervention strategies, responses to intervention strategies, costs associated to individual items and billing procedures. This information can be collected using a portable or handheld device, a personal computer, smartphone or other suitable system. Such information can be collected and stored on a portable device, cloud computing system, database or other suitable storage system.

FIG. 20 illustrates a system or environment 260 which supports the use of a user interface embedded on a computational device(s) software application, a dataset of scores which may or may not be trademarked and/or branded, intervention strategies, and a cloud computing system with online data base in accordance with an embodiment. FIG. 20 also illustrates the flow of information and method of collection of information. As shown in FIG. 20, the user 262 can receive information from the dataset of scores 264, and subsequently carry out an intervention 268. The method of intervention may be collected and/or inputted into the user interface 266 and/or into a cloud computing system, database, on-line blogging website or other suitable system. The user in turn can use 267 these databases/storage systems to aid in future decisions for optimizing interventions.

FIG. 21 illustrates a machine learning system or environment 270, in accordance with an embodiment. As shown in FIG. 21, diagnostic results are automatically collected or manually inputted into the user interface 274 of an embedded software application as shown in "Diagnostic results set 1" 273. The software application algorithmically converts 276 the diagnostic information, with or without the use of an online cloud computing system, into a dataset of scores 280, which may or may not be trademarked and/or branded. The user 271 subsequently carries out an intervention strategy 272. The intervention strategy carried out is automatically collected or manually inputted into the system. A second diagnostic analysis 282 is then carried out on the same individual and the results are again automatically collected or manually inputted into the system. The software application and/or online cloud database may recognize which diagnostic results and/or results from the dataset have changed due to the intervention recorded. The system may then generate new algorithms 278 based on the collected and recorded information with the aim of creating a dataset of scores with the optimum relevance to the interventions. Therefore, presenting data at the point of care with the most meaning towards intervention(s).

FIG. 22 illustrates an automatic invoicing and information collection system or environment 290, in accordance with an embodiment. As shown in FIG. 22, biological sample analysis data 291 can be collected automatically or inputted manually 292 into a user interface 294 or a software application. In addition, interventions 296 carried out, as well as other documentary information 293 can be inputted into the user interface. The user interface may have associated prices for each item entered into the system. A list of the items and prices can then be used for the creation of invoices 298. Invoices may contain prices only or may contain a detailed list of diagnostic results, responses to interventions and other requested information. In addition to diagnostic, documentary and intervention information, information from invoicing can be added to the database which may be stored on a portable device, cloud computing system, or other suitable database 299.

The present invention may be conveniently implemented using one or more conventional general purpose or specialized digital computers or microprocessors programmed according to the teachings of the present disclosure. Appropriate software coding can readily be prepared by skilled programmers based on the teachings of the present disclosure, as will be apparent to those skilled in the software art.

In some embodiments, the present invention includes a computer program product which is a storage medium (media) having instructions stored thereon/in which can be used to program a computer to perform any of the processes of the present invention. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

The foregoing description of the present invention has been provided for the purposes of illustration and description. It is not intended to be exhaustive or to limit the invention to the precise forms disclosed. Many modifications and variations will be apparent to the practitioner skilled in the art. Particularly, while some embodiments of the systems and methods described above are described in the context of equine animals, and portable devices, embodiments of the systems and methods may also be used with other types of non-human and human animals and patients and in various medical and veterinarian settings, and may also be implemented as or used with, for example, websites or similar types of system that provide a user interface to allow medical or veterinarian professionals, patients, or others, to review and manipulate test results, reference points, scores, notes, and other patient information. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A system for analysis of medical and health-related data, for use in optimizing patient-specific intervention strategies using point of care diagnostics, comprising:
   a portable analyzer unit, such as a machine, instrument or reader, that receives a sample associated with a patient and enables an analysis thereof;
   a software application for use in the analysis of the sample, including diagnosis, trend, and intervention evaluation; and
   a database stored at a central or distributed environment, such as at a cloud computing system that enables sharing of patient sample data as received via the portable analyzer unit for use by the software application in analysis and optimizing patient-specific intervention strategies using point of care diagnostics;
   wherein the system operates to receive patient-specific information as data from multiple sources over a period of time, and uses machine learning to identify patterns or trends in the data that are specific to particular patients, including comparing data received at multiple time points with performance measurements of the patients taken at those time points, to determine performance indications for the patients; and
   wherein the software application displays, at a user interface,
      one or more reference points, ranges, or results indicative of a physical status of the patient at various time points, and
      a patient-specific intervention based on the performance measurements of the patient at the various time points, the patient-specific information associated with the patient and collected by the system over the period of time, and the patterns or trends in the data received from the multiple sources.

2. The system of claim 1, wherein the sample associated with the patient is provided via an analysis strip or cartridge which is used to generate data on blood cells, somatic cells, enzymes, proteins, or other body fluid constituents from testing a blood sample, milk sample, or other body fluid sample.

3. The system of claim 2, wherein the system includes that:
   the portable analyzer unit interfaces with and facilitates the testing by the analysis strip or cartridge on the sample.

4. The system of claim 1, wherein the system includes that:
   the software application is installed on a separate computational device such as a smartphone, tablet computer or laptop computer, which can be configured differently for different needs, based on a different understanding of a user's needs.

5. The system of claim 1, wherein the data can be sent and stored on a cloud computing system that
   creates a database of results,
   uses artificial intelligence to design and develop algorithms through machine learning, and
   automatically or regularly synchronizes information with the software application.

6. The system of claim 1, wherein data can be displayed according to the use scenario and includes one or more of results trends and/or custom reference points.

7. The system of claim 1, wherein a user can input information on medical and training interventions under categories of medication, nutrition and/or nutraceuticals, and/or exercise.

8. The system of claim 1, wherein an analysis software or logic includes one or more of a programmed knowledge that
   certain particular characteristics or problems are pertinent to the patient type,
   certain actual blood or other sample analysis information for the current patient are considered indicators of health or performance, and
   certain physiological data for the current patient are considered indicators of health or performance; and
   allows for input and consideration of additional subjective or intuitive information that is pertinent to the intended use case and the current patient.

9. The system of claim 2, wherein a plurality of different types of sample analysis cartridges can be interchangeably used for different animal types, testing requirements, or use cases.

10. The system of claim 1, further comprising
    wherein sampling information can be used as a base reference point or range for subsequent tests on that patient; and
    wherein information about the patient's physical condition at the time of testing can be included to associate the sampling information with physical or environmental conditions; and
    wherein when subsequent tests are performed, deviations of sampling information from established reference points can be determined, to help establish changes in the patient's physical status and/or response to changed physical or environmental conditions such as medical interventions.

11. A method for analysis of medical and health-related data, for use in optimizing patient-specific intervention strategies using point of care diagnostics, comprising the steps of:
    providing a portable analyzer unit, such as a machine or reader, that receives a sample associated with a patient and enables an analysis thereof;
    accessing a software application for use in the analysis of the sample, including diagnosis, trend, and intervention evaluation; and
    using a database stored at a central or distributed environment, such as at a cloud computing system that enables sharing of patient sample data as received via the portable analyzer unit for use by the software application in analysis and optimizing patient-specific intervention strategies using point of care diagnostics, comprising:
    receiving patient-specific information as data from multiple sources over a period of time, and identifying, using machine learning, patterns or trends in the data that are specific to particular patients, including comparing data received at multiple time points with performance measurements of the patients taken at those time points, to determine performance indications for the patients; and displaying, at a user interface,
  one or more reference points, ranges, or results indicative of a physical status of the patient at various time points, and
  a patient-specific intervention based on the performance measurements of the patient at the various time points, the patient-specific information associated with the patient and collected by the system over the period of time, and the patterns or trends in the data received from the multiple sources.

12. The method of claim 11, wherein an analysis software or logic includes one or more of a programmed knowledge that
  certain particular characteristics or problems are pertinent to the patient type,
  certain actual blood or other sample analysis information for the current patient are considered indicators of health or performance, and
  certain physiological data for the current patient are considered indicators of health or performance; and
  allows for input and consideration of additional subjective or intuitive information that is pertinent to the intended use case and the current patient.

13. A non-transitory computer readable medium including instructions stored thereon, which when read and executed by a computer cause the computer to perform the steps comprising:
  providing a portable analyzer unit, such as a machine or reader, that receives a sample associated with a patient and enables an analysis thereof;
  accessing a software application for use in the analysis of the sample, including diagnosis, trend, and intervention evaluation; and
  using a database stored at a central or distributed environment, such as at a cloud computing system that enables sharing of patient sample data as received via the portable analyzer unit for use by the software application in analysis and optimizing patient-specific intervention strategies using point of care diagnostics, comprising:
  receiving patient-specific information as data from multiple sources over a period of time, and identifying, using machine learning, patterns or trends in the data that are specific to particular patients, including comparing data received at multiple time points with performance measurements of the patients taken at those time points, to determine performance indications for the patients; and
  displaying, at a user interface,
    one or more reference points, ranges, or results indicative of a physical status of the patient at various time points, and
    a patient-specific intervention based on the performance measurements of the patient at the various time points, the patient-specific information associated with the patient and collected by the system over the period of time, and the patterns or trends in the data received from the multiple sources.

14. The non-transitory computer readable medium of claim 13, wherein an analysis software or logic includes one or more of a programmed knowledge that
  certain particular characteristics or problems are pertinent to the patient type,
  certain actual blood or other sample analysis information for the current patient are considered indicators of health or performance, and
  certain physiological data for the current patient are considered indicators of health or performance; and
  allows for input and consideration of additional subjective or intuitive information that is pertinent to the intended use case and the current patient.

15. The system of claim 1, wherein the system receives data describing one or more observations associated with the patient, and wherein the software application processes data associated with the biological sample, together with the data describing one or more observations associated with the patient, to cause an output to be displayed via the user interface which includes information describing the patient's current health, status and performance indications.

16. The system of claim 1, wherein the system is configured to identify and characterize at least one of particular patterns or combinations of interventions associated with the patient, and upon, detection of the at least one of particular patterns or combinations, communicate an alert indicative of such detection.

17. The system of claim 1, wherein, for the patient, the system is adapted to:
  at a first time point, receive a first set of diagnostic data, and determine a first score associated with the first set of diagnostic data;
  at a second time point, receive a first set of diagnostic data, and determine a second score associated with the second set of diagnostic data;
  compare the first and second scores, that are associated with the first and second sets of diagnostic data and are determined at the first and second time points, to determine correlations between received diagnostic data and determined scores, for use in determining the one or more performance indications for the particular patient.

18. The system of claim 1, wherein the performance indications for the particular patient and the patient-specific information associated with the particular patient and collected by the system over the period of time are used to reference one or more websites or databases for use in determining a patient-specific intervention for the patient.

19. The system of claim 1, wherein the system receives patient information as biological sample data from the multiple sources, over the period of time, and updates the database in response to receipt of the patient information;
  wherein the software application operates to:
    receive a particular data associated with a biological sample;
    provide the particular data associated with the biological sample, and a user input, for synchronization and storage by the system within the database of patient information, as part of the patient-specific information associated with the particular patient;
    determine, based on analysis of the particular data associated with the biological sample, and the database of patient information including the patient-specific information associated with the particular patient, one or more performance indications for the particular patient; and
  display, at the user interface:
    the one or more performance indications for the particular patient, reference points and ranges including historical results indicative of a physical status of the particular patient at various ones of the time points, and an indication of the particular data associated with the biological sample, in combination with the displayed historical results, and the patient-specific intervention based on the performance indications for the particular patient and the patient-specific information collected by the system over the period of time.

20. The method of claim 11, wherein the software application operates to:

receive a particular data associated with a biological sample, provide the particular data associated with the biological sample, and a user input, for synchronization and storage within the database of patient information, as part of the patient-specific information associated with the particular patient;

determine, based on analysis of the particular data associated with the biological sample, and the database of patient information including the patient-specific information associated with the particular patient, one or more performance indications for the particular patient; and display, at the user interface:

the one or more performance indications for the particular patient, reference points and ranges including historical results indicative of a physical status of the particular patient at various ones of the time points, and an indication of the particular data associated with the biological sample, in combination with the displayed historical results, and the patient-specific intervention based on the performance indications for the particular patient and the patient-specific information collected over the period of time.

* * * * *